(12) United States Patent
Toyoda et al.

(10) Patent No.: US 10,073,080 B2
(45) Date of Patent: Sep. 11, 2018

(54) SAMPLE ANALYZING APPARATUS, DISEASE MONITORING SYSTEM, AND METHOD FOR MANAGING MULTIPLE DISEASE DETERMINATION DATA IN A SAMPLE ANALYZING APPARATUS

(71) Applicant: SYSMEX CORPORATION, Kobe-shi, Hyogo (JP)

(72) Inventors: Akio Toyoda, Kobe (JP); Shinjirou Akamatsu, Kobe (JP)

(73) Assignee: SYSMEX CORPORATION, Kobe-shi (JP)

( * ) Notice: Subject to any disclaimer, the term of this patent is extended or adjusted under 35 U.S.C. 154(b) by 39 days.

(21) Appl. No.: 14/331,386

(22) Filed: Jul. 15, 2014

(65) Prior Publication Data

US 2015/0029508 A1    Jan. 29, 2015

(30) Foreign Application Priority Data

Jul. 23, 2013    (JP) .................................. 2013-152785

(51) Int. Cl.
*G01N 33/49*    (2006.01)
*G01N 35/00*    (2006.01)
(Continued)

(52) U.S. Cl.
CPC ........... *G01N 33/492* (2013.01); *G01N 15/05* (2013.01); *G01N 15/1459* (2013.01);
(Continued)

(58) Field of Classification Search
CPC .. G01N 15/05; G01N 15/1459; G01N 33/492; G01N 33/4915; G01N 35/00871;
(Continued)

(56) References Cited

U.S. PATENT DOCUMENTS 3,916,205 A * 10/1975 Kleinerman ......... G01N 15/147
                                                250/302
4,577,963 A *  3/1986 Traina ................... G01N 15/06
                                                356/28.5
(Continued)

FOREIGN PATENT DOCUMENTS

JP          07-79929 A      3/1995
JP      2003-305010 A     10/2003
(Continued)

OTHER PUBLICATIONS

Mudanyali et al., Integrated rapid-diagnostic-test reader platform on a cellphone, May 17, 2012, Epub, pp. 1-17.*

(Continued)

*Primary Examiner* — Michael P Lapage
(74) *Attorney, Agent, or Firm* — Metrolexis Law Group, PLLC

(57) ABSTRACT

A sample analyzing apparatus comprising a measurement unit configured to measure samples obtained from subjects, an obtaining unit configured to obtain the presence or absence of a disease regarding each sample, a memory in which a measurement result obtained by the measurement unit and the presence or absence of the disease obtained by the obtaining unit are stored in association with the sample, and a communication unit configured to transmit disease information based on the presence or absence of the disease stored in the memory to a receiving apparatus installed in an external facility.

21 Claims, 16 Drawing Sheets

(51) Int. Cl.
*G01N 15/05* (2006.01)
*G01N 15/14* (2006.01)
*G01N 21/53* (2006.01)
*G01N 21/64* (2006.01)
*G01N 15/00* (2006.01)

(52) U.S. Cl.
CPC ......... *G01N 21/53* (2013.01); *G01N 21/6458* (2013.01); *G01N 33/4915* (2013.01); *G01N 35/00871* (2013.01); *G01N 15/1434* (2013.01); *G01N 2015/008* (2013.01); *G01N 2015/0065* (2013.01); *G01N 2015/0073* (2013.01); *G01N 2015/0084* (2013.01); *G01N 2015/055* (2013.01); *G01N 2035/009* (2013.01); *G01N 2035/0091* (2013.01); *G01N 2035/00881* (2013.01); *Y02A 90/22* (2018.01); *Y02A 90/24* (2018.01); *Y02A 90/26* (2018.01)

(58) Field of Classification Search
CPC ........... G01N 21/51; G01N 2015/0065; G01N 2035/009; G01N 2015/008; G01N 2015/0084; G01N 2015/055; G01N 2035/00881; G01N 2035/0091; G01N 15/1434; G01N 2015/0073
See application file for complete search history.

(56) References Cited

U.S. PATENT DOCUMENTS

| | | | | |
|---|---|---|---|---|
| 7,892,850 | B2 * | 2/2011 | Oguni | ................ G01N 33/5094 356/73 |
| 2005/0002826 | A1 | 1/2005 | Oguni et al. | |
| 2007/0008492 | A1 * | 1/2007 | Kaido | .................... A61B 3/032 351/239 |
| 2008/0208832 | A1 * | 8/2008 | Friedlander | ....... G06F 17/30522 |
| 2010/0052915 | A1 * | 3/2010 | Allen | ..................... A61B 5/411 340/573.1 |
| 2010/0070197 | A1 * | 3/2010 | Wang | ........................ G01J 3/02 702/22 |
| 2011/0179405 | A1 * | 7/2011 | Dicks | ........................ G06F 8/61 717/168 |
| 2011/0190030 | A1 * | 8/2011 | Glynn | ..................... H04M 1/00 455/556.1 |
| 2012/0108917 | A1 * | 5/2012 | Libbus | ................. A61B 5/0006 600/301 |
| 2012/0242501 | A1 * | 9/2012 | Tran | ..................... A61B 5/0024 340/870.02 |
| 2014/0135588 | A1 * | 5/2014 | Al-Ali | ................... G06F 19/327 600/300 |
| 2015/0323461 | A1 * | 11/2015 | Chan | ................. G01N 21/6428 506/9 |

FOREIGN PATENT DOCUMENTS

| | | |
|---|---|---|
| JP | 2007-200107 A | 8/2007 |
| JP | 2011-128935 A | 6/2011 |
| WO | 2009/136573 A1 | 11/2009 |

OTHER PUBLICATIONS

Chin et al., Lab-on-a-chip devices for global healh: Past studies and future opportunities, Oct. 27, 2006, Lab Chip, pp. 41-51.*

Robert Johnson, Screening Test to Detect Chlamydia trachomatis and Neisseria gonorrhoeae Infections, Oct. 18, 2002, CDC, MMWR, pp. 1-41.*

Onur Mudanyali et al., Integrated Rapid-Diagnostic-Test Reader Platform on a Cellphone, Lab Chip, Aug. 7, 2012 (Cited in Office Action issued Sep. 23, 2016 in counterpart Chinese application).

* cited by examiner

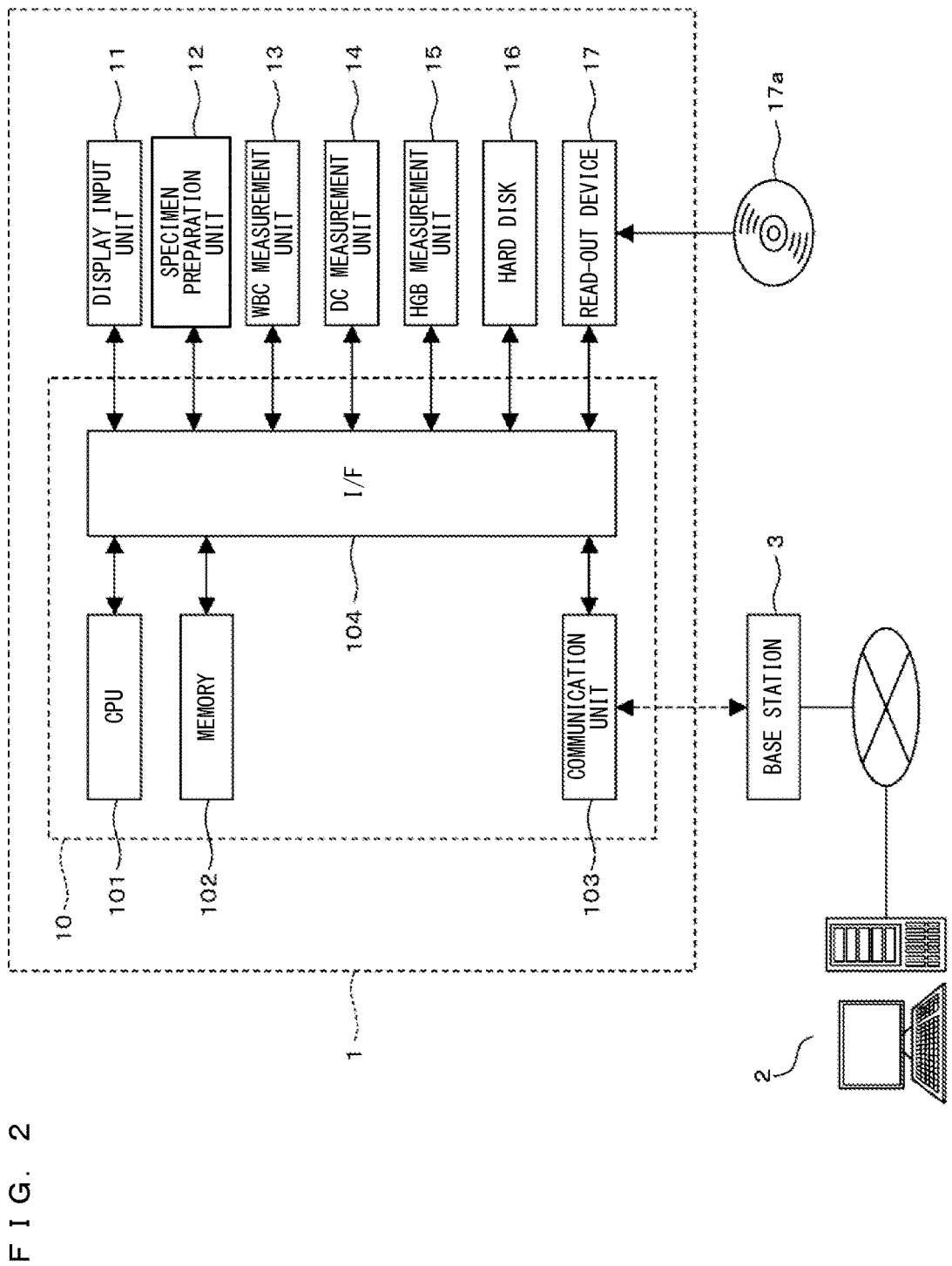
F I G. 2

F I G. 6A    RESULT TABLE

| SAMPLE ID | WBC (×10²/μL) | ... | PLT (×10⁴/μL) | ... | MEASUREMENT DATE AND TIME | HIV | TB | MALARIA | INPUT DATE AND TIME | TRANS-MISSION |
|---|---|---|---|---|---|---|---|---|---|---|
| 0001 | 85 | ... | 17.6 | ... | 2013/06/03 10:05 | + | ? | ? | 2013/06/03 13:05 | DONE |
| 0002 | 76 | ... | 21.2 | ... | 2013/06/03 10:15 | − | − | − | 2013/06/03 13:07 | DONE |
| 0003 | 89 | ... | 18.0 | ... | 2013/06/03 10:20 | + | − | ? | | |
| 0004 | 87 | ... | 17.9 | ... | 2013/06/03 10:25 | + | − | + | 2013/06/04 11:15 | |
| 0005 | 86 | ... | 18.1 | ... | 2013/06/03 10:30 | ? | + | − | 2013/06/04 11:17 | |
| 0006 | 74 | ... | 17.1 | ... | 2013/06/03 10:30 | | | ? | 2013/06/04 11:19 | |
| 0007 | 82 | ... | 20.1 | ... | 2013/06/03 10:30 | | | | | |

F I G. 6B    TRANSMISSION INFORMATION

| IDENTIFICATION INFORMATION | HIV THE NUMBER OF POSITIVE SAMPLES | HIV THE TOTAL NUMBER OF SAMPLES | TB THE NUMBER OF POSITIVE SAMPLES | TB THE TOTAL NUMBER OF SAMPLES | MALARIA THE NUMBER OF POSITIVE SAMPLES | MALARIA THE TOTAL NUMBER OF SAMPLES | INPUT DATE |
|---|---|---|---|---|---|---|---|
| A001 | 243 | 397 | 32 | 380 | 30 | 385 | 2013/06/04 |

SAMPLE ID 0003 --- D11

MEASUREMENT
DATE AND   2013/06/03 10:20
TIME

| WBC  | ... | W-SCR  | ... | NEUT#  | ... |
| RBC  | ... | W-MCR  | ... | LYMPH# | ... |
| HGB  | ... | W-LCR  | ... | MONO#  | ... |
| HCT  | ... | RDW-SD | ... | EO#    | ... |
| MCV  | ... | RDW-CV | ... | BASO#  | ... |
| MCH  | ... | PDW    | ... | NEUT%  | ... |
| MCHC | ... | MPV    | ... | LYMPH% | ... |
| PLT  | ... | P-LCR  | ... | MONO%  | ... |
|      |     |        |     | EO%    | ... |
|      |     |        |     | BAS0%  | ... |

D12

HIV       [POSITIVE] --- D13       (POSITIVE) D13a  (NEGATIVE) D13b  (NOT TESTED) D13c
TB        [NEGATIVE] --- D14       (POSITIVE) D14a  (NEGATIVE) D14b  (NOT TESTED) D14c
MALARIA   [NOT TESTED] --- D15     (POSITIVE) D15a  (NEGATIVE) D15b  (NOT TESTED) D15c (TEMPORARY SAVE) D16    (THREE MAJOR DISEASES INFORMATION INPUT COMPLETE) D17

SAMPLE ID 0003 --- D21

MEASUREMENT
DATE AND   2013/06/03 10:20
TIME

| WBC  | ... | W-SCR  | ... | NEUT#  | ... |
| RBC  | ... | W-MCR  | ... | LYMPH# | ... |
| HGB  | ... | W-LCR  | ... | MONO#  | ... |
| HCT  | ... | RDW-SD | ... | EO#    | ... |
| MCV  | ... | RDW-CV | ... | BASO#  | ... |
| MCH  | ... | PDW    | ... | NEUT%  | ... |
| MCHC | ... | MPV    | ... | LYMPH% | ... |
| PLT  | ... | P-LCR  | ... | MONO%  | ... |
|      |     |        |     | EO%    | ... |
|      |     |        |     | BAS0%  | ... |

D22

INPUT DATE  2013/06/04 11:15
AND TIME

HIV       POSITIVE
TB        NEGATIVE
MALARIA   NOT TESTED

D23

(CLOSE) D24

FIG. 8A

IDENTIFICATION TABLE

| IDENTIFICATION INFORMATION | FACILITY NAME | LOCATION |
|---|---|---|
| A001 | CLINIC A1 | SOKOTO |
| A002 | CLINIC A2 | SOKOTO |
| A003 | CLINIC A3 | SOKOTO |
| B001 | CLINIC B1 | KANO |
| B002 | CLINIC B2 | KANO |
| B003 | CLINIC B3 | KANO |
| C001 | CLINIC C1 | GOMBE |
| C002 | CLINIC C2 | GOMBE |
| C003 | CLINIC C3 | GOMBE |

FIG. 8B

RECEPTION TABLE

| IDENTIFICATION INFORMATION | HIV THE NUMBER OF POSITIVE SAMPLES | HIV THE TOTAL NUMBER OF SAMPLES | TB THE NUMBER OF POSITIVE SAMPLES | TB THE TOTAL NUMBER OF SAMPLES | MALARIA THE NUMBER OF POSITIVE SAMPLES | MALARIA THE TOTAL NUMBER OF SAMPLES | INPUT DATE |
|---|---|---|---|---|---|---|---|
| A001 | 243 | 397 | 32 | 380 | 30 | 385 | 2013/06/04 |
| A002 | 245 | 387 | 31 | 375 | 27 | 390 | 2013/06/04 |
| A003 | 263 | 321 | 28 | 320 | 25 | 335 | 2013/06/04 |
| B001 | 8 | 120 | 70 | 108 | 7 | 110 | 2013/06/04 |
| B002 | 31 | 395 | 291 | 387 | 25 | 370 | 2013/06/04 |
| B003 | 23 | 320 | 228 | 321 | 20 | 315 | 2013/06/04 |
| C001 | 24 | 380 | 12 | 395 | 234 | 397 | 2013/06/04 |
| C002 | 5 | 85 | 3 | 80 | 54 | 90 | 2013/06/04 |
| C003 | 21 | 315 | 9 | 330 | 251 | 321 | 2013/06/04 |

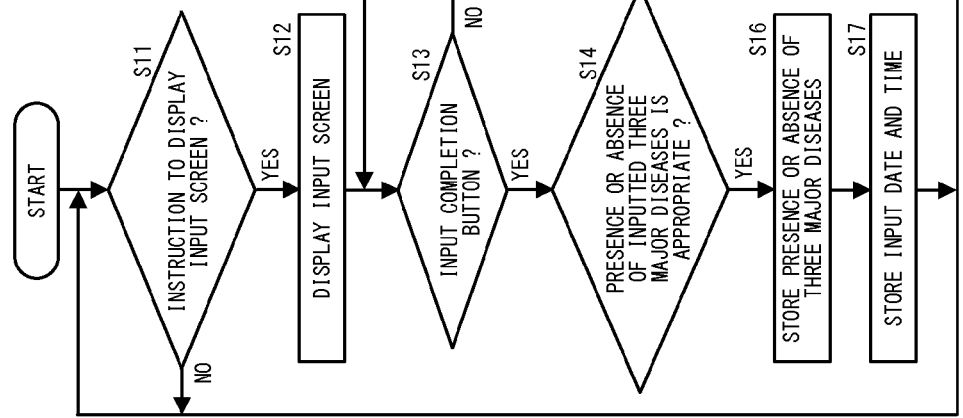
FIG. 9B INPUT PROCESS
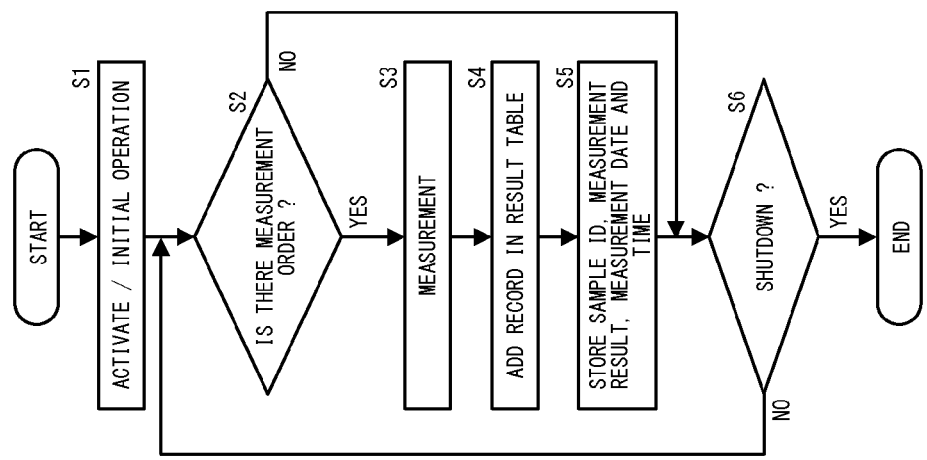
FIG. 9A MEASUREMENT PROCESS

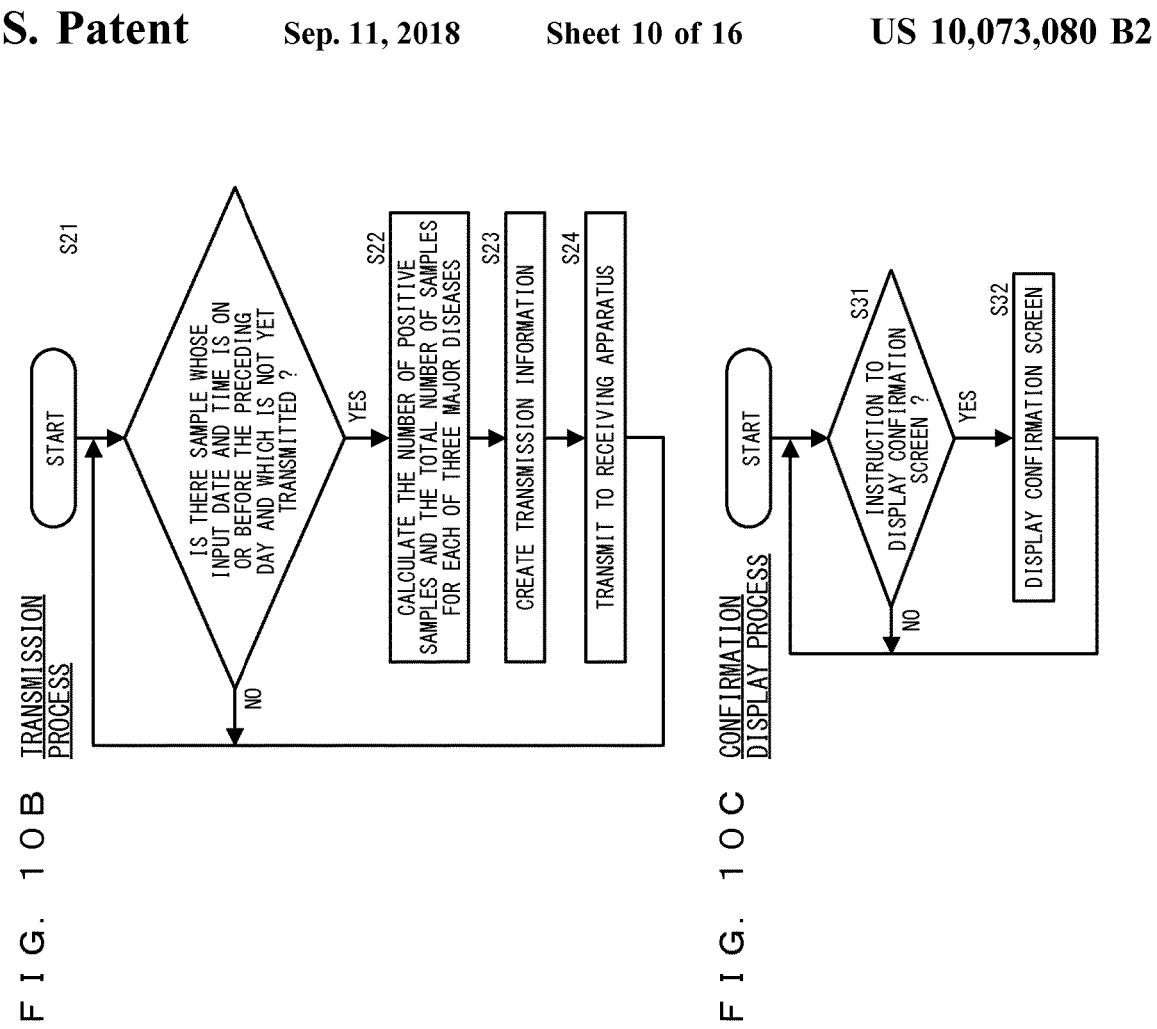
FIG. 10B TRANSMISSION PROCESS
FIG. 10C CONFIRMATION DISPLAY PROCESS
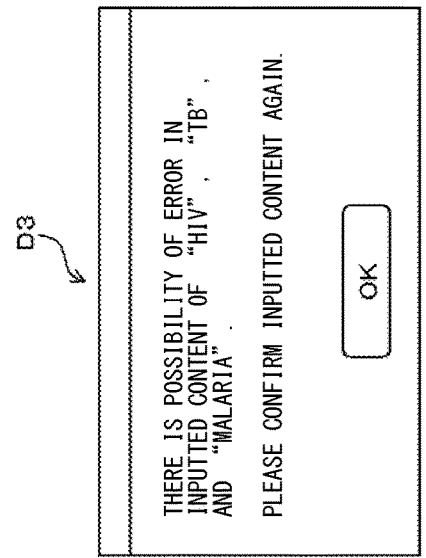
FIG. 10A

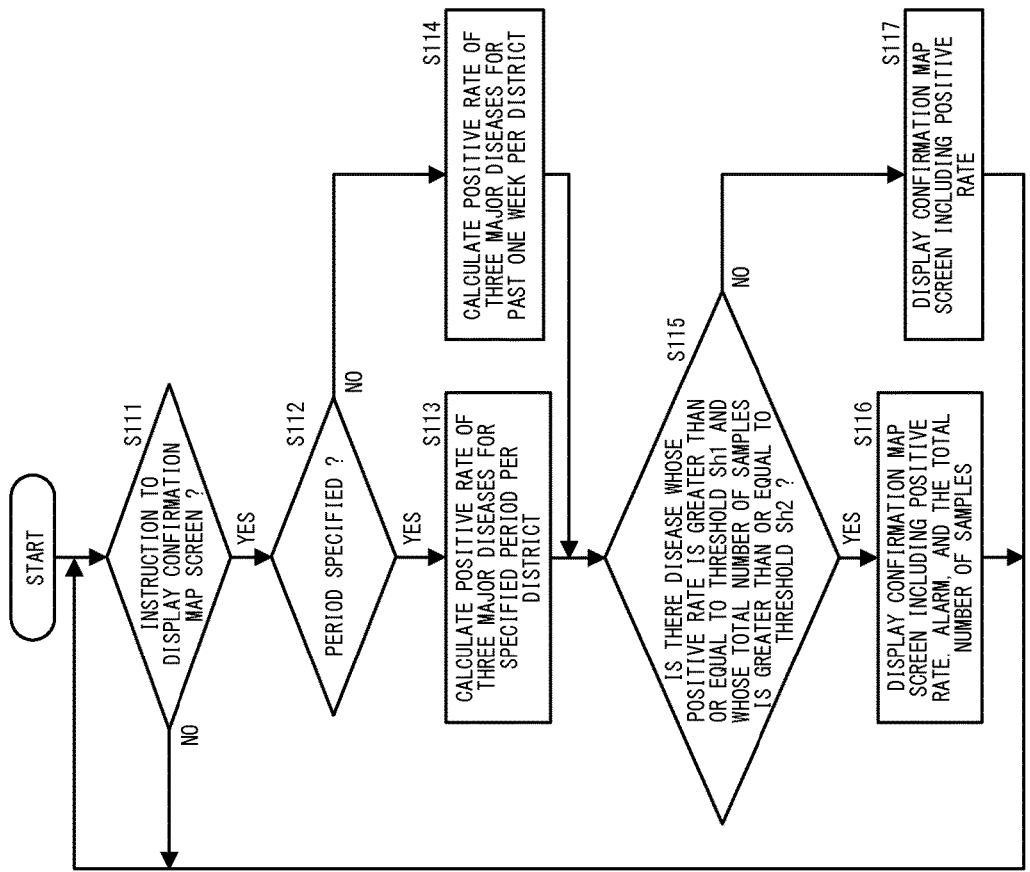
FIG. 11B  TOTALING AND DISPLAYING PROCESS
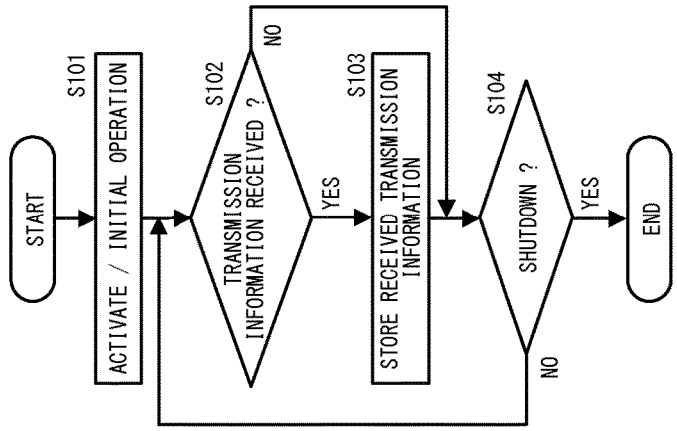
FIG. 11A  RECEPTION PROCESS FIG. 14A
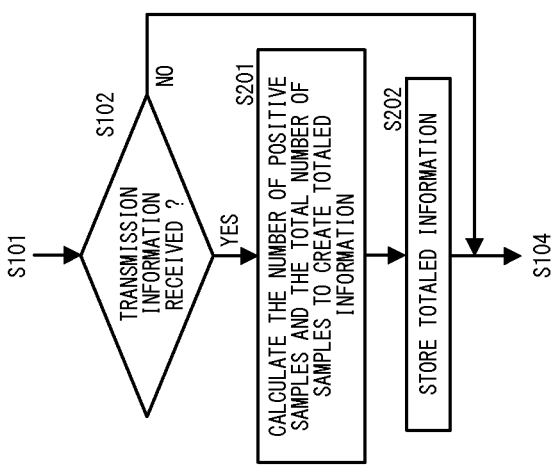
FIG. 14B MEASUREMENT PROCESS
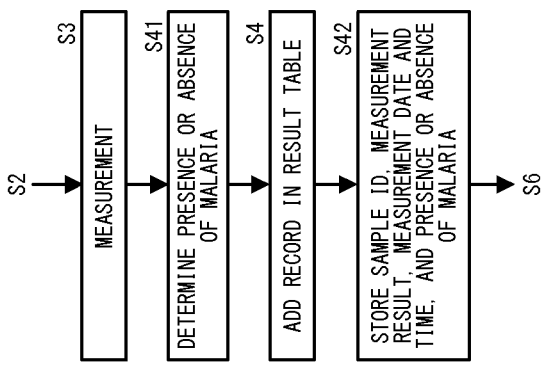
FIG. 14D RECEPTION PROCESS
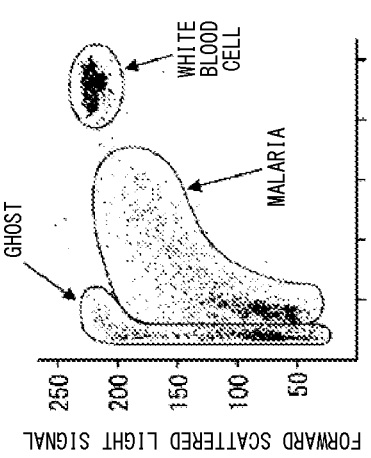
FIG. 14C TRANSMISSION INFORMATION
| IDENTIFICATION INFORMATION | SAMPLE ID | WBC ($\times 10^2/\mu L$) | ... | PLT ($\times 10^4/\mu L$) | ... | MEASUREMENT DATE AND TIME | HIV | TB | MALARIA | INPUT DATE AND TIME |
|---|---|---|---|---|---|---|---|---|---|---|
| A001 | 0003 | 89 | ... | 18.0 | ... | 2013/06/03 10:20 | + | − | ? | 2013/06/04 11:15 |
| A001 | 0004 | 87 | ... | 17.9 | ... | 2013/06/03 10:25 | + | − | + | 2013/06/04 11:17 |
| A001 | 0005 | 86 | ... | 18.1 | ... | 2013/06/03 10:30 | ? | − | − | 2013/06/04 11:19 |

F I G. 1 5 A   RESULT TABLE

| SAMPLE ID | SEX | AGE | WBC (×10²/μL) | ... | MEASUREMENT DATE AND TIME | HIV | TB | MALARIA | INPUT DATE AND TIME | TRANS- MISSION |
|---|---|---|---|---|---|---|---|---|---|---|
| 0001 | MALE | 35 | 85 | ... | 2013/06/03 10:05 | + | ? | ? | 2013/06/03 13:05 | DONE |
| 0002 | FEMALE | 26 | 76 | ... | 2013/06/03 10:15 | − | − | − | 2013/06/03 13:07 | DONE |
| 0003 | MALE | 14 | 89 | ... | 2013/06/03 10:20 | + | − | ? | 2013/06/04 11:15 | |
| 0004 | MALE | 55 | 87 | ... | 2013/06/03 10:25 | + | − | + | 2013/06/04 11:17 | |
| 0005 | FEMALE | 41 | 86 | ... | 2013/06/03 10:30 | ? | + | − | 2013/06/04 11:19 | |
| 0006 | FEMALE | 52 | 74 | ... | 2013/06/03 10:30 | | | ? | | |
| 0007 | MALE | 23 | 82 | ... | 2013/06/03 10:30 | | | | | |

F I G. 1 5 B   TRANSMISSION INFORMATION

| IDENTIFICA- TION INFORMATION | HIV THE NUMBER OF POSITIVE SAMPLES | MALE | AVERAGE AGE | FEMALE | AVERAGE AGE | HIV THE TOTAL NUMBER OF SAMPLES | MALE | AVERAGE AGE | FEMALE | AVERAGE AGE | ... | INPUT DATE AND TIME |
|---|---|---|---|---|---|---|---|---|---|---|---|---|
| A001 | 243 | 116 | 34.2 | 127 | 38.3 | 397 | 195 | 36.2 | 202 | 40.7 | | 2013/06/04 |

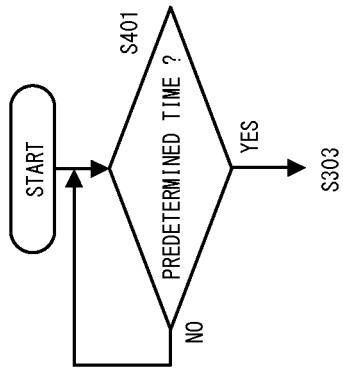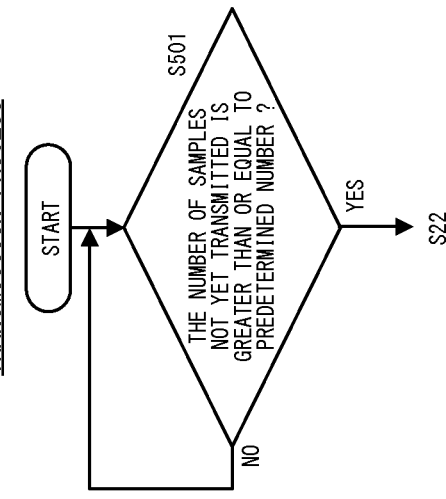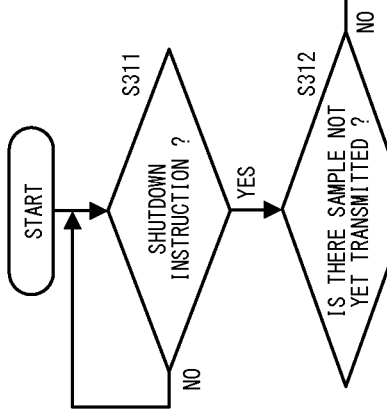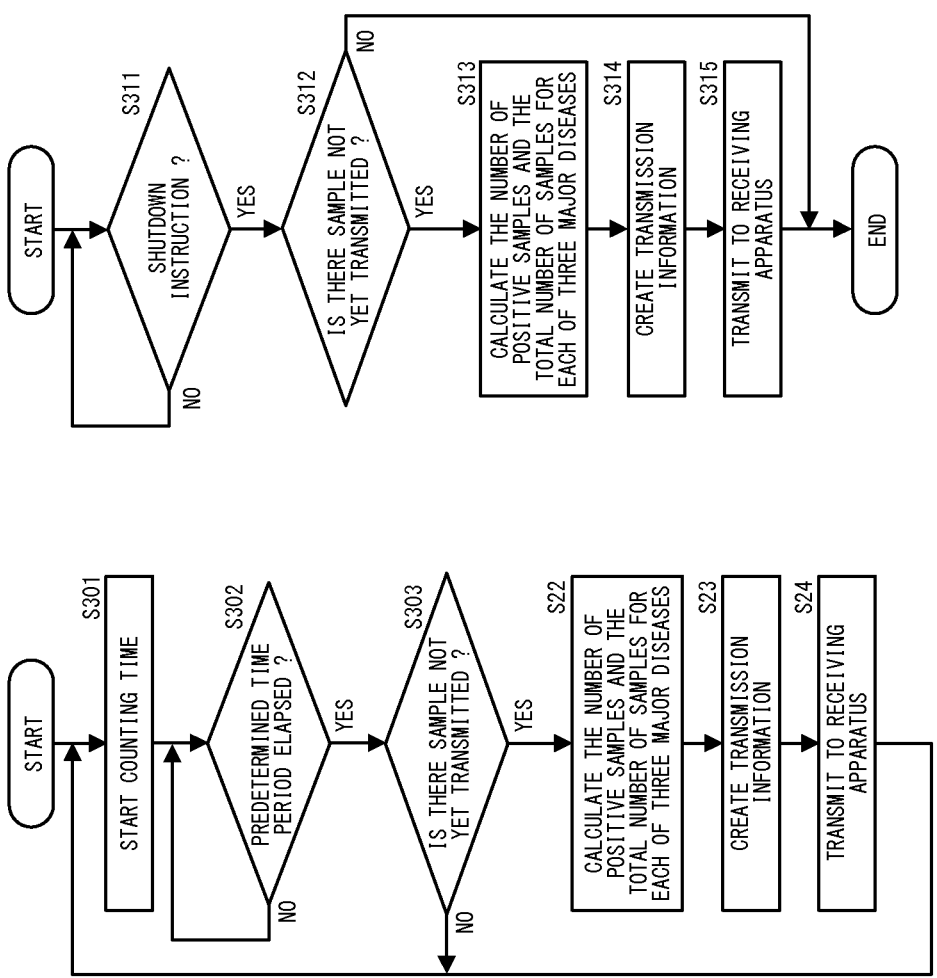

SAMPLE ANALYZING APPARATUS, DISEASE MONITORING SYSTEM, AND METHOD FOR MANAGING MULTIPLE DISEASE DETERMINATION DATA IN A SAMPLE ANALYZING APPARATUS

FIELD OF THE INVENTION

The present invention relates to a sample analyzing apparatus which analyzes samples collected from subjects, a method for managing data of the sample analyzing apparatus, and a disease monitoring system including the sample analyzing apparatus.

BACKGROUND

At present, so-called three major infectious diseases such as HIV/AIDS, tuberculosis (TB), and malaria are problems in developing countries and emerging countries such as those in Africa, in particular. Among these infectious diseases, diagnosis of HIV/AIDS is known to be performed by use of a dedicated measurement apparatus which counts the number of CD4-positive lymphocytes contained in a blood sample. Diagnoses of TB and malaria are known to be manually performed by use of a fluorescence microscope. In addition, it is known that diagnosis of malaria can be performed also by use of a sample analyzing apparatus that can detect malaria-infected red blood cells in a blood sample (see International Publication WO 2009/136573).

As described above, diagnoses of the three major infectious diseases are performed individually by use of different apparatuses, respectively, and thus, diagnosis results of the respective infectious diseases tend to be managed separately.

Moreover, when infection to the three major infectious diseases has occurred, it is required not only to take countermeasures for the infected individuals but also to promptly take, as a district, countermeasures such as disinfection of relevant facilities. Thus, the states of infection to the three major infectious diseases need to be provided promptly and efficiently to an agency that controls the district.

SUMMARY OF THE INVENTION

The scope of the present invention is defined solely by the appended claims, and is not affected to any degree by the statements within this summary.

A first aspect of the present invention is a sample analyzing apparatus comprising a measurement unit configured to measure samples obtained from subjects, an obtaining unit configured to obtain the presence or absence of a disease regarding each sample, a memory in which a measurement result obtained by the measurement unit and the presence or absence of the disease obtained by the obtaining unit are stored in association with the sample, and a communication unit configured to transmit disease information based on the presence or absence of the disease stored in the memory to a receiving apparatus installed in an external facility.

A second aspect of the present invention is a method for managing data of a sample analyzing apparatus which comprises a measurement unit configured to measure a sample, and a memory, the method comprising, measuring, by use of the measurement unit, a sample obtained from a subject, obtaining the presence or absence of a disease regarding the sample, storing, in the memory, an obtained measurement result and the presence or absence of the disease, in association with the sample, and transmitting disease information based on the presence or absence of the disease to a receiving apparatus installed in an external facility.

BRIEF DESCRIPTION OF THE DRAWINGS

FIG. 2 shows a configuration of a sample analyzing apparatus according to the embodiment;

FIG. 6A illustrates a concept of a configuration of a result table according to the embodiment and FIG. 6B illustrates a concept of a configuration of a transmission information according to the embodiment;

FIG. 7A shows a configuration of an input screen according to the embodiment and FIG. 7B shows a configuration of a confirmation screen according to the embodiment;

FIG. 8A illustrates a concept of a configuration of an identification table according to the embodiment and FIG. 8B illustrates a concept of a configuration of a reception table according to the embodiment;

FIG. 9A shows a flow chart of a measurement process according to the embodiment and FIG. 9B shows a flow chart of an input process performed by the sample analyzing apparatus according to the embodiment;

FIG. 10A shows an alarm screen according to the embodiment. FIG. 10B shows a flow chart of a transmission process performed by the sample analyzing apparatus, and FIG. 10C shows a flow chart of a confirmation display process performed by the sample analyzing apparatus;

FIG. 11A shows a flow chart of a reception process according to the embodiment and FIG. 11B shows a flow chart of a totaling and displaying process performed by the receiving apparatus according to the embodiment;

FIG. 14A shows a scattergram created when the presence or absence of malaria is determined according to a modification, FIG. 14B shows a flow chart showing a measurement process performed by the sample analyzing apparatus according to a modification, FIG. 14C shows a concept of a configuration of transmission information according to a modification, and FIG. 14D shows a flow chart showing a reception process performed by the receiving apparatus, according to a modification;

FIG. 15A illustrates a concept of a configuration of a result table according to a modification and FIG. 15B illustrates a concept of a configuration of transmission information according to a modification; and FIG. 16A, FIG. 16B, FIG. 16C, and FIG. 16D show flow charts of transmission processes according to modifications.

DETAILED DESCRIPTION OF THE PREFERRED EMBODIMENTS

The preferred embodiments of the present invention will be described hereinafter with reference to the drawings.

The present embodiment is obtained by applying the present invention to a sample analyzing apparatus for counting blood cells in blood and to a disease monitoring system including the sample analyzing apparatus. Hereinafter, the sample analyzing apparatus and the disease monitoring system according to the present embodiment will be described with reference to the drawings.

Figure 1:
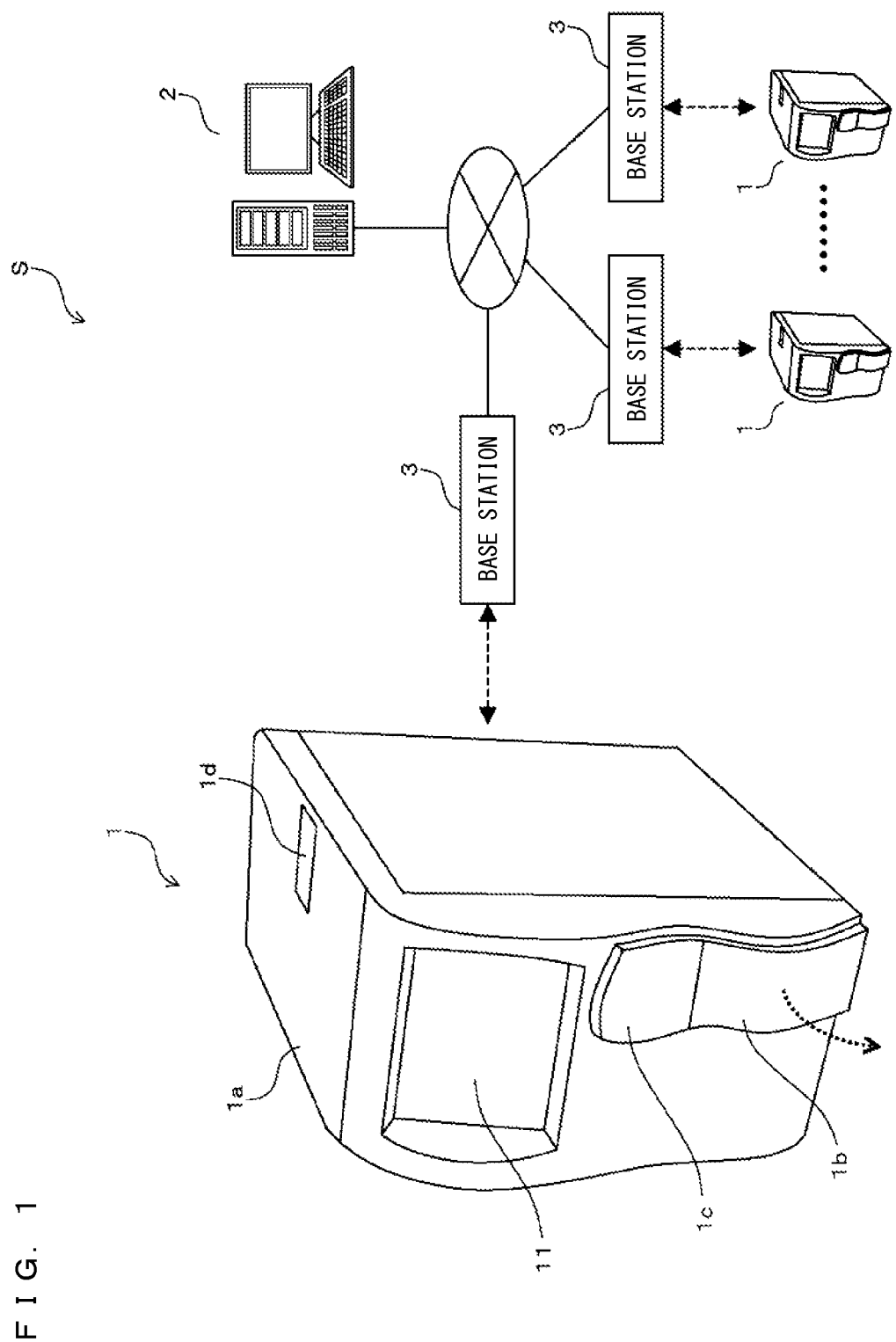
FIG. 1 shows an external view of a sample analyzing apparatus and a configuration of a disease monitoring system according to an embodiment.

FIG. 1 shows an external view of a sample analyzing apparatus 1 and a configuration of a disease monitoring system S according to the present embodiment.

The disease monitoring system S is used by an agency, such as a government agency, that comprehensively controls/manages medical care in districts, in order to monitor the infection states of HIV/AIDS, tuberculosis (TB), and malaria (hereinafter, referred to as "three major diseases") in that country. The disease monitoring system S includes the sample analyzing apparatuses 1 installed at respective hospitals and test facilities in the country, and a receiving apparatus 2 which manages test results of the three major diseases obtained by these sample analyzing apparatuses 1.

Each sample analyzing apparatus 1 includes a communication unit 103 (see FIG. 2) capable of performing wireless communication, and is configured to be able to perform wireless communication with a base station 3 nearby. It should be noted that the wireless communication in the present embodiment is realized by WiMAX (Worldwide Interoperability for Microwave Access). Thus, even in a case where the sample analyzing apparatus 1 is away from the base station 3 by several tens of kilometers, wireless communication can be performed. Moreover, the receiving apparatus 2 and each base station 3 are connected to the Internet network, and are configured to be able to perform communication with each other. Accordingly, the sample analyzing apparatus 1 is communicably connected to the receiving apparatus 2.

The components (see FIG. 2) of the sample analyzing apparatus 1 are housed in a housing 1a. The front face of the housing 1a is provided with a display input unit 11 being a touch panel-type display, a sample setting panel 1b, and a button 1c for opening and closing the sample setting panel 1b. The top face of the housing 1a is provided with an opening 1d through which a paper sheet having a measurement result printed thereon is discharged.

Before starting measurement by the sample analyzing apparatus 1, an operator presses the button 1c to open the sample setting panel 1b into the direction indicated by the dotted arrow. In a state where the sample setting panel 1b is open, the operator sets a sample container in a sample setting unit (not shown) inside the sample setting panel 1b. Then, the operator presses the button 1c to close the sample setting panel 1b, and then, inputs an instruction to start measurement via the display input unit 11. Accordingly, in the sample analyzing apparatus 1, measurement is performed on the sample in the sample container. The operator can cause the display input unit 11 to display a measurement result obtained through the measurement, and can cause a paper sheet having the measurement result printed thereon to be discharged from the opening 1d.

The operator can input, via the display input unit 11, the presence or absence of the three major diseases obtained by external apparatuses different from the sample analyzing apparatus 1, and can cause the sample analyzing apparatus 1 to store the presence or absence of the three major diseases. The sample analyzing apparatus 1 transmits the stored presence or absence of the three major diseases to the receiving apparatus 2 as appropriate. Input and the like of the presence or absence of the three major diseases will be described later with reference to FIG. 5 and thereafter.

FIG. 2 shows a configuration of the sample analyzing apparatus 1.

The sample analyzing apparatus 1 includes, in addition to the display input unit 11 shown in FIG. 1, a substrate 10, a specimen preparation unit 12, a WBC measurement unit 13, a DC measurement unit 14, a HGB measurement unit 15, a hard disk 16, and a read-out device 17. The substrate 10 includes a CPU 101, a memory 102 implemented by a ROM and a RAM, the communication unit 103, and an interface (I/F) 104. The CPU 101 is connected to components of the sample analyzing apparatus 1 via the interface 104. The CPU 101 executes computer programs stored in the memory 102 and the hard disk 16. Moreover, the CPU 101 controls components of the sample analyzing apparatus 1 and receives signals from components of the sample analyzing apparatus 1 to process them. As described above, the communication unit 103 is configured to be able to perform wireless communication with a base station 3 nearby.

The specimen preparation unit 12 includes a plurality of chambers (not shown) for mixing a sample with a reagent and a diluent, and prepares a measurement specimen to be used in measurement. The specimen preparation unit 12 transfers the measurement specimen prepared by use of the chambers to the WBC measurement unit 13, the DC measurement unit 14, and the HGB measurement unit 15. The WBC measurement unit 13 includes a flow cell L1, and is configured to be able to measure white blood cells in the measurement specimen by a flow cytometry using laser light.

Figure 3:
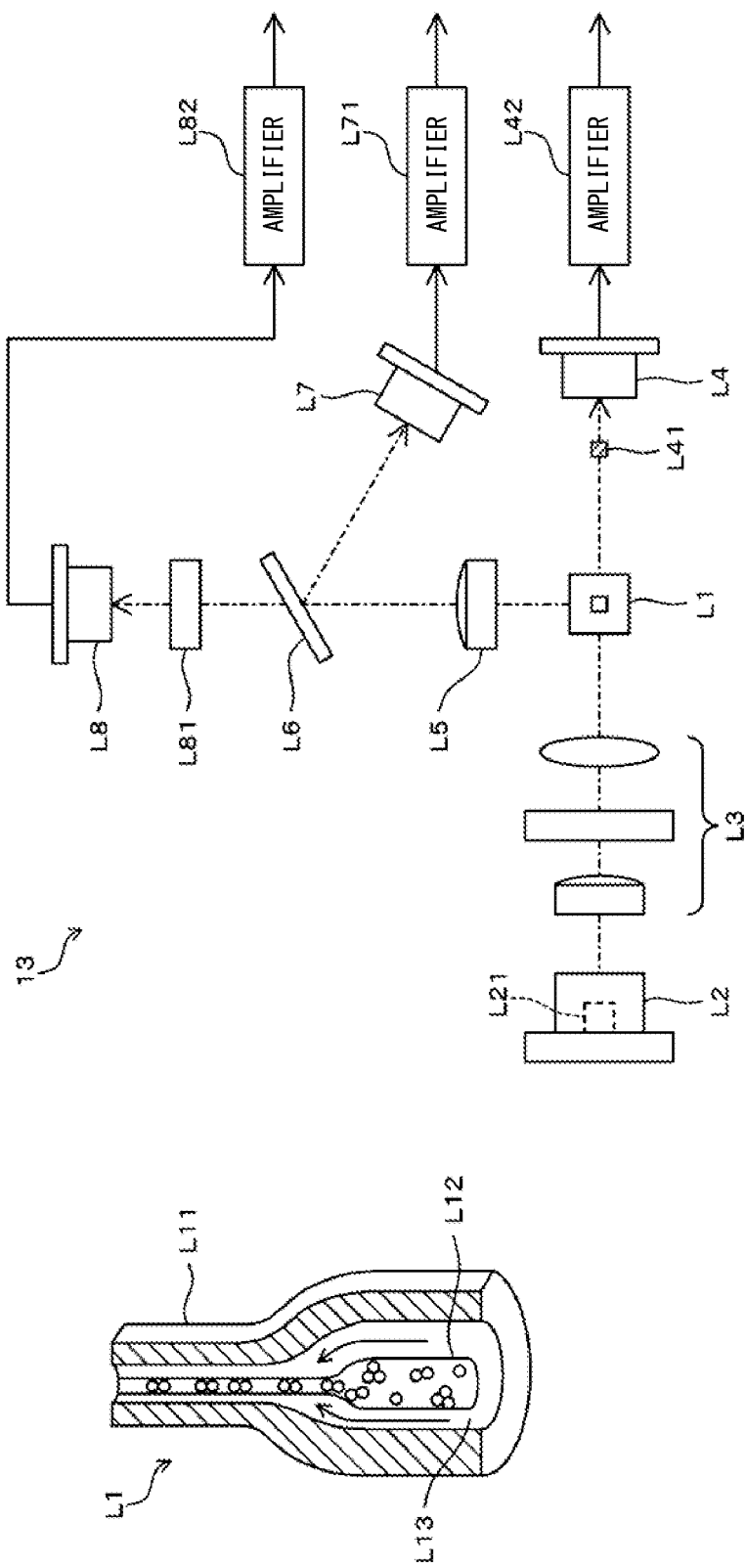
FIG. 3A schematically shows a configuration of a flow cell according to the embodiment and FIG. 3B schematically shows a configuration of a WBC measurement unit according to the embodiment.

FIG. 3A schematically shows a configuration of the flow cell L1.

The flow cell L1 is structured in a tube shape by a translucent material such as quartz, glass, or synthetic resin, and the inside thereof serves as a flow path in which a measurement specimen and a sheath liquid flow. The flow cell L1 is provided with an orifice L11 whose inner space is made narrower than the other portion. The vicinity of the inlet of the orifice L11 has a double tube structure, and the inner tube portion serves as a specimen nozzle L12. The outer space of the specimen nozzle L12 is a flow path L13 in which the sheath liquid flows. The sheath liquid flows in the flow path L13 to be introduced into the orifice L11. The sheath liquid supplied to the flow cell L1 flows so as to surround the measurement specimen discharged from the specimen nozzle L12. Then, the flow of the measurement specimen is narrowed into a thin flow by the orifice L11, and particles such as white blood cells and red blood cells contained in the measurement specimen pass through the orifice L11, one by one, while being surrounded by the sheath liquid.

FIG. 3B schematically shows a configuration of the WBC measurement unit 13.

A semiconductor laser L2 includes a laser element L21, and the laser element L21 emits a violet laser beam whose wavelength is about 405 nm. The laser beam emitted from the semiconductor laser L2 is applied to the orifice L11 of the flow cell L1. Between the semiconductor laser L2 and the flow cell L1, an irradiation lens system L3 composed of a plurality of lenses is arranged. By the irradiation lens system L3, the laser beam emitted from the semiconductor laser L2 is converged into a beam spot.

On the optical axis of the laser beam emitted from the semiconductor laser L2, a beam stopper L41 is provided so as to be opposed to the irradiation lens system L3, relative to the flow cell L1. The beam stopper L41 shields direct light from the semiconductor laser L2. To the downstream of the beam stopper L41, a photodiode L4 is arranged. The photodiode L4 is configured to receive forward scattered light of the laser beam occurring at the measurement specimen that is flowing in the flow cell L1. The photodiode L4 outputs a forward scattered light signal based on the received forward scattered light. An amplifier L42 amplifies the forward scattered light signal to be outputted to the CPU 101.

On a side relative to the flow cell L1 and in a direction orthogonal to the optical axis of the laser beam emitted from the semiconductor laser L2, a side condenser lens L5 is arranged. The side condenser lens L5 condenses side light that occurs when a blood cell passing through the flow cell L1 is irradiated with the laser beam. To the downstream of the side condenser lens L5, a dichroic mirror L6 is arranged. The dichroic mirror L6 is configured to separate side light that has passed through the side condenser lens L5 into side scattered light and side fluorescence.

To a side relative to the dichroic mirror L6, a photodiode L7 for receiving side scattered light is arranged. The photodiode L7 outputs a side scattered light signal based on the received side scattered light. An amplifier L71 amplifies the side scattered light signal to be outputted to the CPU 101. To the downstream of the dichroic mirror L6, an optical filter L81 having wavelength selectivity and an avalanche photodiode L8 for receiving side fluorescence are arranged. The avalanche photodiode L8 outputs a side fluorescence signal based on side fluorescence having been subjected to wavelength selection by the optical filter L81. An amplifier L82 amplifies the side fluorescence signal to be outputted to the CPU 101.

With reference back to FIG. 2, the DC measurement unit 14 includes a flow cell (not shown), and to this flow cell, the measurement specimen prepared by the specimen preparation unit 12 is transferred. The DC measurement unit 14 is configured to be able to measure a red blood cell count (RBC) and a platelet count (PLT) by a sheath flow DC detection method. The DC measurement unit 14 is also configured to be able to obtain measurement data for calculating a hematocrit value (HCT) by a red-blood-cell pulse height detection. Further, the DC measurement unit 14 is also used for detecting a white blood cell count (WBC) for calculating a lymphocyte ratio.

The HGB measurement unit 15 includes a cell (not shown) for containing a diluted specimen, and into this cell, the measurement specimen prepared by the specimen preparation unit 12 is transferred. The HGB measurement unit 15 is configured to able to measure a hemoglobin amount (HGB) by a methemoglobin method. Moreover, the HGB measurement unit 15 includes a light emitting diode (not shown), and the light emitting diode emits light whose wavelength is about 555 nm. The HGB measurement unit 15 irradiates the measurement specimen in the cell with light from the light emitting diode, thereby measuring absorbance of the measurement specimen.

Measurement data obtained by the WBC measurement unit 13, the DC measurement unit 14, and the HGB measurement unit 15 is processed by the CPU 101 to be stored in the hard disk 16. The hard disk 16 has stored therein a computer program for analyzing measurement data. The CPU 101 executes this computer program to analyze the measurement data, thereby calculating a white blood cell count (WBC), a red blood cell count (RBC), a hemoglobin amount (HGB), a hematocrit value (HCT), a mean corpuscular volume (MCV), a mean corpuscular hemoglobin (MCH), a mean cell hemoglobin concentration (MCHC), a platelet count (PLT), and the like. Moreover, the CPU 101 creates a scattergram by use of forward scattered light signals, side scattered light signals, and side fluorescence signals, and classifies white blood cells into five groups, i.e., neutrophil (NEUT), lymphocyte (LYMPH), monocyte (MONO), eosinophil (EO), and basophil (BASO). The measurement result of blood cells obtained through the above calculation and classification is stored in the hard disk 16.

Moreover, the hard disk 16 has stored therein a computer program for receiving an input of the presence or absence of the three major diseases made by the operator via the display input unit 11. The inputted presence or absence of the three major diseases is stored in the hard disk 16. Further, the hard disk 16 has stored therein a computer program for displaying the measurement result and the presence or absence of the three major diseases on the display input unit 11, and a computer program for creating transmission information described later and for transmitting the created transmission information to the receiving apparatus 2. The read-out device 17 is implemented by a CD drive, a DVD drive, or the like and can read out computer programs and data stored in a storage medium 17a. It should be noted that, by storing, into the hard disk 16, computer programs and data stored in the storage medium 17a, new functions can be added to the sample analyzing apparatus 1.

Figure 4:
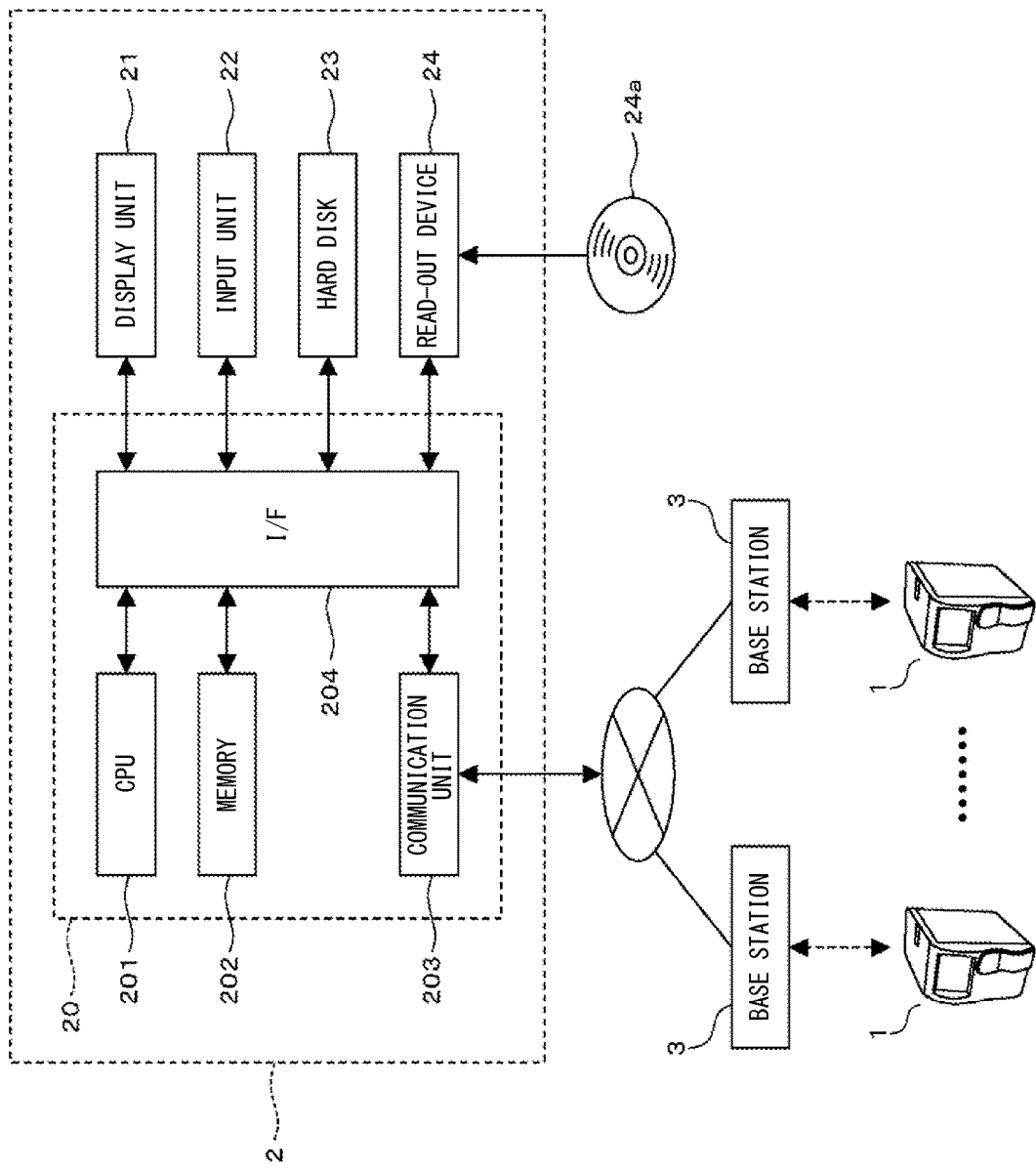
FIG. 4 shows a configuration of a receiving apparatus according to the embodiment.

FIG. 4 shows a configuration of the receiving apparatus 2.

The receiving apparatus 2 includes a substrate 20, a display unit 21, an input unit 22, a hard disk 23, and a read-out device 24. The substrate 20 includes a CPU 201, a memory 202 implemented by a ROM and a RAM, a communication unit 203, and an interface (I/F) 204. The CPU 201 is connected to components of the receiving apparatus 2 via the interface 204. The CPU 201 executes computer programs stored in the memory 202 and the hard disk 23. Moreover, the CPU 201 controls components of the receiving apparatus 2 and receives signals from components of the receiving apparatus 2 to process them. The communication unit 203 is communicably connected to a plurality of the base stations 3 via the Internet network.

The display unit 21 displays an image based on a signal from the CPU 201. The input unit 22 transmits, to the CPU 201, a signal inputted from an operator of the receiving apparatus 2. In the hard disk 23, transmission information transmitted from the sample analyzing apparatus 1 is stored. The hard disk 23 has stored therein a computer program for totaling stored transmission information and for displaying the totaled result and the like on the display unit 21. The read-out device 24 is implemented by a CD drive, a DVD drive, or the like, and can read out computer programs and data stored in a storage medium 24a. It should be noted that, by storing, into the hard disk 23, computer programs and data stored in the storage medium 24a, new functions can be added to the receiving apparatus 2.

Figure 5:
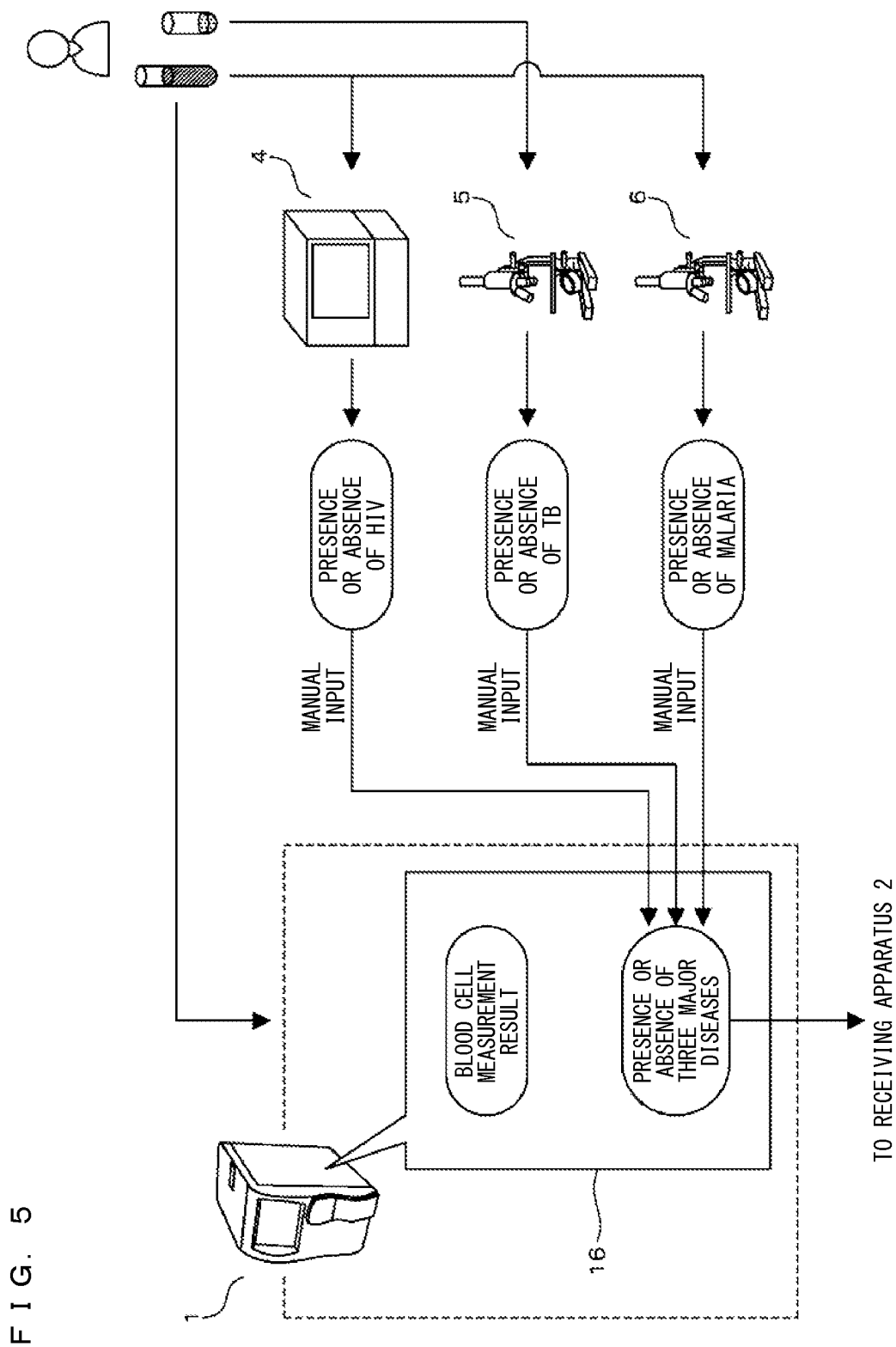
FIG. 5 shows the routes in which the presence or absence of three major diseases is stored in the sample analyzing apparatus according to the embodiment.

FIG. 5 shows the routes in which the presence or absence of the three major diseases is stored in the sample analyzing apparatus 1.

In each facility included in the disease monitoring system S, along with one sample analyzing apparatus 1, an apparatus 4 for diagnosing and monitoring HIV/AIDS (hereinafter, simply referred to as "HIV"), a fluorescence microscope 5 for diagnosing TB, and a fluorescence microscope 6 for diagnosing malaria are set. A blood sample collected from a subject is provided to the sample analyzing apparatus 1, the apparatus 4, and the fluorescence microscope 6. Moreover, sputum collected from this subject is provided to the fluorescence microscope 5.

In the apparatus 4, a measurement specimen prepared from the blood sample is flowed in the flow cell. Then, the measurement specimen flowing in a line is irradiated with a laser beam, and generated scattered light and fluorescence are each measured by a PMT (photomultiplier). At this time, the number of CD4-positive lymphocytes in the measurement specimen is counted, and the number of CD4-positive lymphocytes (the number in 1 μL) is displayed on a display unit of the apparatus 4. When the displayed number of CD4-positive lymphocytes is lower than a predetermined threshold, the operator determines that the subject has HIV. One example of a criterion for HIV-positive is that the number of CD4-positive lymphocytes is less than or equal to 500/μL.

In the fluorescence microscope 5, sputum that is stained and smeared on a slide glass is observed. When acid-fast bacilli are detected through this observation, there is a high possibility that the subject has TB, and thus, the operator determines that the subject has TB. In the fluorescence microscope 6, a blood sample that is stained and smeared on a slide glass is observed. When Plasmodium parasites in red blood cells are detected through this observation, the operator determines that the subject has malaria.

When measurement is performed in the sample analyzing apparatus 1, as descried above, a measurement result of blood cells is stored in the hard disk 16. On the other hand, the operator stores, in the hard disk 16 via the display input unit 11 (by manual input), a diagnosis result (the presence or absence of HIV) obtained by the apparatus 4, a diagnosis result (the presence or absence of TB) obtained by use of the fluorescence microscope 5, and a diagnosis result (the presence or absence of malaria) obtained by use of the fluorescence microscope 6. In the sample analyzing apparatus 1, the presence or absence of HIV, the presence or absence of TB, and the presence or absence of malaria (the presence or absence of the three major diseases) that are stored in the hard disk 16 are totaled, respectively, and transmission information (see FIG. 6B) created through the totaling is transmitted to the receiving apparatus 2.

FIG. 6A illustrates a concept of a configuration of a result table stored in the hard disk 16 of the sample analyzing apparatus 1.

The result table includes, per sample ID for identifying a subject, a measurement result performed in the sample analyzing apparatus 1, a measurement date and time when the measurement was performed, the presence or absence of the three major diseases, an input date and time of the three major diseases, and a transmission status. The measurement result includes results of a plurality of measurement items performed in the sample analyzing apparatus 1. The presence or absence of the three major diseases includes the presence or absence of HIV, the presence or absence of TB, and the presence or absence of malaria which were inputted by the operator. In the present embodiment, as the presence or absence of a disease, when positive, "+" is stored, when negative, "−" is stored, and when no test was performed, "?" is stored.

Immediately after measurement has been performed in the sample analyzing apparatus 1, that is, when the presence or absence of the three major diseases has not yet been inputted by the operator, as shown in sample ID "0007", only a measurement result, and a measurement date and time are stored, and the presence or absence of the three major diseases, the input date and time of the three major diseases, and the transmission status remain blank. From this state, when input of the presence or absence of the three major diseases is completed, as shown in sample IDs "0003" to "0005", the presence or absence of the three major diseases and an input date and time of the three major diseases are stored.

Of the presence or absence of the three major diseases, when the presence or absence of only a part of the diseases has been inputted, any of "+", "−", and "?" is stored only in the presence or absence of the corresponding diseases. For example, when only the presence or absence of TB and the presence or absence of malaria have been inputted, as shown in sample ID "0006", the presence or absence of HIV and the input date and time remain blank. From this state, when the presence or absence of HIV is inputted, the presence or absence of the three major diseases is now all inputted, and the date and time at this time is stored in the input date and time.

When the presence or absence of the three major diseases is all inputted, and the input date and time is stored, the sample analyzing apparatus 1 totals the presence or absence of each of the three major diseases as appropriate, and creates transmission information. Then, when the transmission information is transmitted to the receiving apparatus 2, "DONE" is stored in the transmission status of each sample included in this transmission information.

FIG. 6B illustrates a concept of a configuration of transmission information created in the sample analyzing apparatus 1.

The transmission information includes: identification information for identifying a facility where the sample analyzing apparatus 1 that has created this transmission information is installed; the number of samples (the number of positive samples), for each disease, for which the presence or absence is "+"; the number of samples (the total number of samples), for each disease, for which the presence or absence is "+" or "−"; and an input date indicated by the input date and time of the samples included in this transmission information. The identification information is stored in advance in the hard disk 16, for each sample analyzing apparatus 1 as unique information thereof. The transmission information is created, based on the result table, by totaling, among samples whose input dates and times are stored and whose transmission statuses are blank, the presence or absence for each of the three major diseases of samples of the same day.

FIG. 7A shows a configuration of an input screen D1 to be displayed on the display input unit 11 of the sample analyzing apparatus 1. The input screen D1 regarding the three major diseases is displayed when the operator specifies a sample ID and gives an instruction to display the input screen D1.

The input screen D1 includes: an area D11 for indicating a sample ID; an area D12 for indicating a measurement date and time and a measurement result performed by the sample analyzing apparatus 1; areas D13 to D15; buttons D13a to D13c, D14a to D14c, and D15a to D15c; a temporary save button D16; and an input completion button D17.

The operator inputs the presence or absence of HIV obtained by the apparatus 4, by pressing the button D13a to D13c. In the area D13, in accordance with the button D13a to D13c that has been pressed, the presence or absence of HIV is displayed. Further, the operator inputs the presence or absence of TB obtained by use of the fluorescence microscope 5, by pressing the button D14a to D14c. In the area D14, in accordance with the button D14a to D14c that has been pressed, the presence or absence of TB is displayed. Further, the operator inputs the presence or absence of malaria obtained by use of the fluorescence microscope 6, by pressing the button D15a to D15c. In the area D15, in accordance with the button D15a to D15c that has been pressed, the presence or absence of malaria is displayed.

By pressing the temporary save button D16, the operator can save the state in which the presence or absence of only a part of diseases among the three major diseases is inputted. Accordingly, for example, as shown in sample ID "0006" in FIG. 6A, the presence or absence of only a part of diseases is temporarily saved. By inputting the presence or absence of all the three major diseases and then pressing the input completion button D17, the operator can save the presence or absence of the three major diseases and the input date and time. Accordingly, for example, as shown in sample IDs "0003" to "0005" in FIG. 6A, the presence or absence of all the diseases is stored, and the date and time when the input completion button D17 was pressed is stored as the input date and time.

FIG. 7B shows a configuration of a confirmation screen D2 to be displayed on the display input unit 11 of the sample analyzing apparatus 1. The confirmation screen D2 is displayed when the operator specifies a sample ID and gives an instruction to display the confirmation screen D2.

The confirmation screen D2 includes: areas D21 and D22 similar to those in the input screen D1 regarding the three major diseases; an area D23 for indicating the input date and time and the presence or absence of the three major diseases; and a button D24 for closing the confirmation screen D2. By causing the confirmation screen D2 to be displayed, the operator can confirm the measurement result and the presence or absence of the three major diseases of the specified sample, arranged side by side on one screen. It should be noted that in a case where the presence or absence of only a part of diseases among the three major diseases has been inputted, the input date and time and the presence or absence of diseases that has not yet been inputted in the area D23 remain blank.

FIG. 8A illustrates a concept of a configuration of an identification table stored in the hard disk 23 of the receiving apparatus 2. The identification table includes: identification information for identifying a facility where the sample analyzing apparatus 1 is installed; the name of this facility; and the location of this facility. The identification information corresponds to identification information stored in the hard disk 16 of each sample analyzing apparatus 1.

FIG. 8B illustrates a concept of a configuration of a reception table stored in the hard disk 23 of the receiving apparatus 2. The reception table includes the same items as the items included in the transmission information shown in FIG. 6B. In the reception table, transmission information transmitted from each sample analyzing apparatus 1 is sequentially stored.

FIG. 9A is a flow chart showing a measurement process performed by the sample analyzing apparatus 1.

When an operator has given an activation instruction, the CPU 101 of the sample analyzing apparatus 1 activates each component of the sample analyzing apparatus 1, and performs an initial operation for setting a state where measurement can be performed (S1). Accordingly, an input process (see FIG. 9B), a transmission process (see FIG. 10B), and a confirmation display process (see FIG. 10C) which are described later are started. Subsequently, the CPU 101 determines whether there is a measurement order (S2). A measurement order is created by, for example, the operator inputting a sample ID and items for measurement to be performed in the sample analyzing apparatus 1, via the display input unit 11 of the sample analyzing apparatus 1.

When there is a measurement order (S2: YES), the CPU 101 causes a measurement specimen to be prepared from a sample as descried above, and causes the WBC measurement unit 13, the DC measurement unit 14, and the HGB measurement unit 15 to perform measurement of the sample (S3). Then, the CPU 101 adds a record (line) in the result table (S4), and stores, into this record, the sample ID, the measurement result, and the measurement date and time (S5). As a result, for example, a state shown in sample ID "0007" in FIG. 6A is made. The processes of S2 to S5 are repeated until a shutdown instruction is given (S6).

FIG. 9B is a flow chart showing the input process performed by the sample analyzing apparatus 1.

When the operator has specified a sample ID and given an instruction to display the input screen D1, via the display input unit 11 (S11: YES), the CPU 101 causes the display input unit 11 to display the input screen D1 (S12). When the input screen D1 has been displayed, the operator inputs, as descried above, the presence or absence of the three major diseases obtained from the apparatus 4 and the fluorescence microscopes 5 and 6, by pressing the buttons D13a to D13c, D14a to D14c, and D15a to D15c, as appropriate.

When the operator has pressed the input completion button D17 (S13: YES), the CPU 101 determines, based on a predetermined measurement result obtained by the sample analyzing apparatus 1 and being displayed in the area D12 of the input screen D1, whether the inputted presence or absence of the three major diseases is appropriate or not (S14). Specifically, in a case where the inputted presence or absence of a disease is positive, when the value of a predetermined measurement item is away from an expected range of values of the predetermined measurement item when the disease is positive, it is determined that the inputted presence or absence (positive) of the disease is incorrect. Similarly, in a case where the inputted presence or absence of the disease is negative, when the value of the predetermined measurement item is away from an expected range of values of the predetermined measurement item when the disease is negative, it is determined that the inputted presence or absence (negative) of the disease is incorrect.

For example, when a subject has HIV, WBC (white blood cell count) decreases. Thus, in a case where appropriateness of the inputted presence or absence of HIV is to be determined, WBC is used as the predetermined measurement item. When a subject has TB, WBC (white blood cell count) decreases. Thus, in a case where appropriateness of the inputted presence or absence of TB is to be determined, WBC is used as the predetermined measurement item. When a subject has malaria, PLT (platelet count) decreases. Thus, in a case where appropriateness of the inputted presence or absence of malaria is to be determined, PLT is used as the predetermined measurement item.

When the inputted presence or absence of the three major diseases is not appropriate (S14: NO), the CPU 101 causes the display input unit 11 to display an alarm screen D3 shown in FIG. 10A (S15), and returns the process to S13. On the alarm screen D3, the disease for which the inputted presence or absence has been determined as inappropriate is displayed, and an instruction that urges the operator to confirm the inputted content again is displayed. FIG. 10A illustrates an example case where the inputs for all the diseases were inappropriate. Then, upon the alarm screen D3 being closed, the CPU 101 returns the process to S13. On the other hand, when the inputted presence or absence of the three major diseases is appropriate (S14: YES), the CPU 101 stores the presence or absence of the three major diseases into the record for the corresponding sample ID in the result table (S16), and stores the input date and time (S17). Then, the CPU 101 closes the input screen D1 and returns the process to S11.

When the operator has pressed the temporary save button D16 (S13: NO, S18: YES), the CPU 101 stores the contents of the areas D13 to D15 on the input screen D1 into the record of the corresponding sample ID in the result table (S19), closes the input screen D1, and returns the process to S11.

FIG. 10B is a flow chart showing the transmission process performed by the sample analyzing apparatus 1.

The CPU 101 determines, with reference to the result table, whether there is a sample whose input date and time is on or before the preceding day relative to the current date and time and which has not yet been transmitted (the transmission status is blank) (S21). With reference to FIG. 6A, for example, in a case where the current date and time is "2013/06/05 09:00", samples whose input dates and times are on or before the preceding day and which have not yet been transmitted are sample IDs "0003" to "0005".

When there are samples whose input dates and times are on or before the preceding day and which have not yet been transmitted (S21: YES), the CPU 101 calculates, with regard to these samples, the number of positive samples and the total number of samples for each of the three major diseases (S22). Specifically, when the presence or absence of a disease is "+", the number of positive samples of the disease is increased by one, and when a presence or absence of the disease is "+" or "−", the total number of samples of the disease is increased by one.

Subsequently, the CPU 101 adds the identification information of this sample analyzing apparatus 1 and the input date obtained from the input date and time of the samples for which the calculation was performed, to the number of positive samples and the total number of samples each calculated for each of the three major diseases. Thereby, the CPU 101 creates transmission information as shown in FIG. 6B (S23). Then, the CPU 101 transmits the created transmission information to the receiving apparatus 2 (S24), and returns the process to S21.

FIG. 10C is a flow chart showing the confirmation display process performed by the sample analyzing apparatus 1.

When the operator has specified a sample ID and given an instruction to display the confirmation screen D2, via the display input unit 11 (S31: YES), the CPU 101 causes the display input unit 11 to display the confirmation screen D2 (S32). When the button D24 is pressed, the CPU 101 returns the process to S31.

FIG. 11A is a flow chart showing a reception process performed by the receiving apparatus 2.

When an operator of the receiving apparatus 2 has given an activation instruction, the CPU 201 of the receiving apparatus 2 activates each component of the receiving apparatus 2, and performs an initial operation for setting a state where processing can be performed (S101). Accordingly, a totaling and displaying process (see FIG. 11B) described later is started. Subsequently, upon receiving transmission information transmitted from the sample analyzing apparatus 1 (S102: YES), the CPU 201 stores the received transmission information in the reception table (S103). The processes of S102 and S103 are repeated until a shutdown instruction is given.

FIG. 11B is a flow chart showing the totaling and displaying process performed by the receiving apparatus 2.

When the operator gives, via the input unit 22, an instruction to display a confirmation map screen D4 (S111: YES), the CPU 201 determines whether a period has been specified by the operator (S112).

When the period has been specified (S112: YES), the CPU 201 refers to the reception table and the identification table, and calculates, based on the specified period, the number of positive samples and the number of negative samples of the three major diseases per district (for each location of the sample analyzing apparatus 1), and calculates a positive rate (in total) (S113). On the other hand, when the period has not been specified (S112: NO), the CPU 201 calculates the number of positive samples and the number of negative samples of the three major diseases per district, for a past one week as a default period, and calculates a positive rate (in total) (S114). The positive rate is obtained for each disease, through calculation of "the number of positive samples of the target disease/(the number of positive samples of the target disease+the number of negative samples of the target disease)".

Specifically, for example, in a case where the specified period is "2013/05/28 to 2013/06/04", only records (lines) having input dates included in this period are extracted from the reception table. Then, based on the identification information of the extracted records, locations are obtained from the identification table. In a case where the reception table is in the state as shown in FIG. 8B, the records whose identification information is "A001", "A002", and "A003" all have "Sokoto" as the location, and are considered as being in the same district. Then, among the extracted records based on the specified period, with regard to the records of the same district, calculation is performed for each of the three major diseases.

Subsequently, the CPU 201 determines whether there is a disease whose positive rate calculated in S113 or S114 is greater than or equal to a threshold Sh1 and whose total number of samples is greater than or equal to a threshold Sh2 (S115). The thresholds Sh1 and Sh2 are stored in advance in the hard disk 23 of the receiving apparatus 2, and in the present embodiment, they are set as 60% and 800, respectively. It should be noted that the threshold Sh1 is set as appropriate in accordance with a criterion that determines an epidemic state, and the threshold Sh2 is set as appropriate to a value that makes the calculated positive rate reliable.

When having determined as YES in S115, the CPU 201 causes the display unit 21 to display the confirmation map screen D4 (see FIG. 12) including the calculated positive rates, an alarm indicating that a corresponding disease is in an epidemic state, and the total number of samples of the corresponding disease (S116). On the other hand, when having determined as NO in S115, the CPU 201 causes the display unit 21 to display the confirmation map screen D4 including the calculated positive rates (S117). When an end instruction has been inputted on the confirmation map screen D4, the confirmation map screen D4 is closed and the process is returned to S111.

Figure 12:
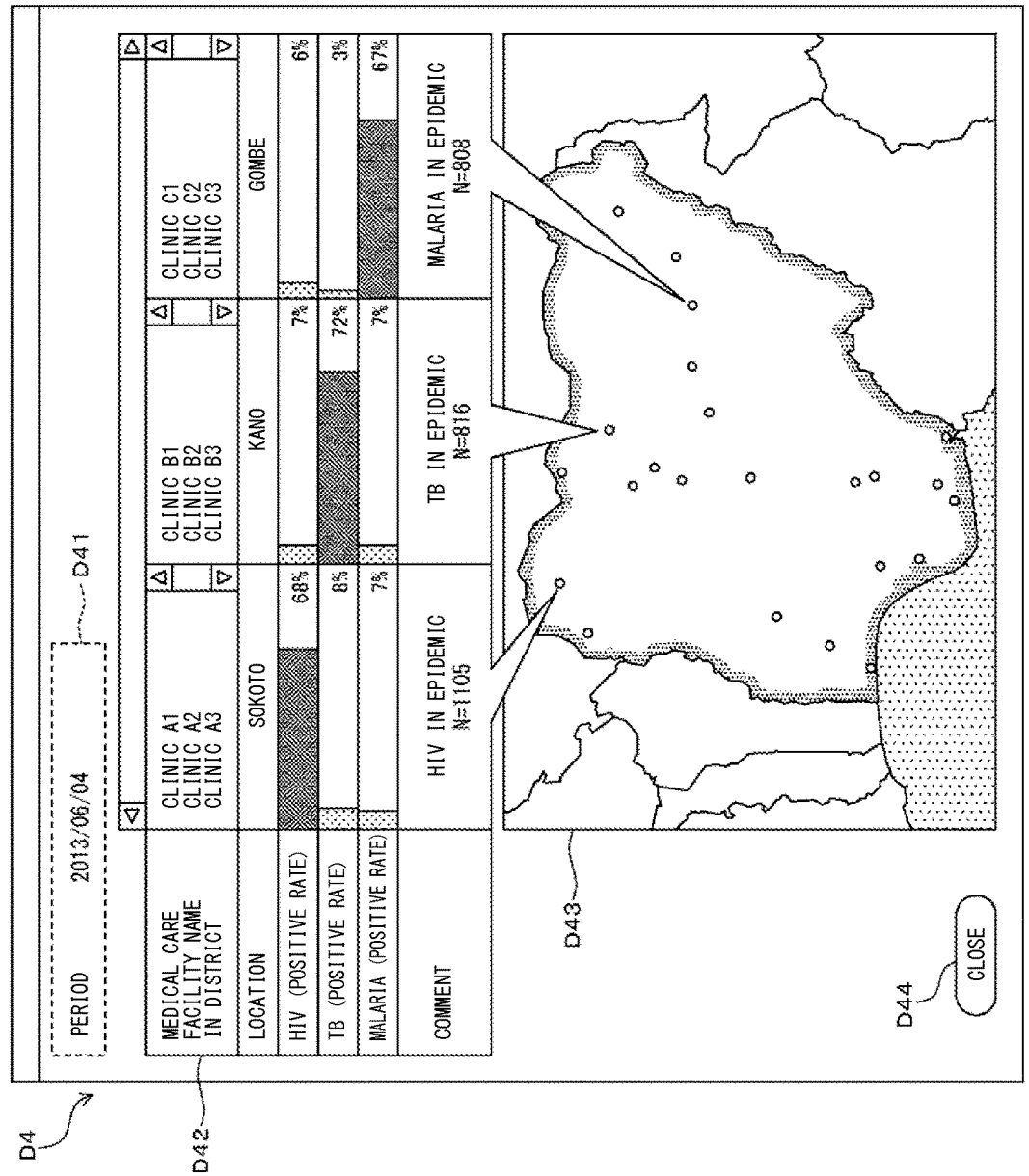
FIG. 12 shows a configuration of a confirmation map screen according to the embodiment.

FIG. 12 shows a configuration of the confirmation map screen D4 to be displayed on the display unit 21 of the receiving apparatus 2. FIG. 12 illustrates an example case where only the information (nine records) shown in FIG. 8B is stored in the reception table and the specified date is "2013/06/04".

The confirmation map screen D4 includes an area D41 for indicating the period based on which the totaling was performed in S113 and S114 in FIG. 11B, a table D42 showing the totaled contents, a map D43 showing districts, and a button D44 for closing the confirmation map screen D4. The table D42 includes, per district (location), facility names included in the district, the positive rates of the respective three major diseases calculated in the period shown in the area D41, bar graphs that allow visual understanding of the positive rates, and comments regarding information of epidemic. In the table D42 of this case, information regarding Sokoto being the location of clinics A1 to A3, information regarding Kano being the location of clinics B1 to B3, and information regarding Gombe being the location of clinics C1 to C3 are displayed.

In each comment in the table D42, an alarm indicating that, among the three major diseases calculated for each district, a disease whose positive rate is greater than or equal to the threshold Sh1 and whose total number of samples is greater than or equal to the threshold Sh2 is in an epidemic state, and the total number of samples of this disease are displayed. In the map D43, a map of the entirety of the districts (the country in the case of the present embodiment) to be monitored by the disease monitoring system S is displayed. At this time, districts for which alarms are displayed in the table D42 are also shown on the map.

As described above, according to the present embodiment, in the hard disk 16, the measurement result of blood cells obtained by the sample analyzing apparatus 1, and the presence or absence of the three major diseases obtained by the apparatus 4, and the fluorescence microscopes 5 and 6 are stored in association with the sample. Therefore, by comparing the measurement result with the presence or absence of the three major diseases as appropriate, the morbidity state of the patient can be appropriately determined. Moreover, transmission information created based on the presence or absence of the three major diseases is transmitted to the receiving apparatus 2. Therefore, for example, in a case where the receiving apparatus 2 is installed in an agency, such as a government agency, that comprehensively controls the districts, the sample analyzing apparatus 1 can promptly and efficiently provide the controlling agency with transmission information created based on the presence or absence of the three major diseases.

According to the present embodiment, the operator can store, via the input screen D1, the presence or absence of the three major diseases into the hard disk 16 of the sample analyzing apparatus 1. Thus, the sample analyzing apparatus 1 becomes able to obtain the presence or absence of the three major diseases obtained from the apparatus 4 and the fluorescence microscopes 5 and 6 which are external apparatuses.

According to the present embodiment, transmission information includes identification information for identifying the facility where the sample analyzing apparatus 1 that created this transmission information is installed, and the presence or absence of the three major diseases, and the sample analyzing apparatus 1 transmits the transmission information to the receiving apparatus 2 via the communication unit 103. Accordingly, the receiving apparatus 2 can obtain the infection states of the three major diseases for each district.

According to the present embodiment, the sample analyzing apparatus 1 includes the communication unit 103 capable of performing wireless communication. Thus, even in a case where the facility where the sample analyzing apparatus 1 is installed is not provided with communication infrastructures for connecting to the Internet network, the transmission information totaled in this sample analyzing apparatus 1 can be transmitted to the receiving apparatus 2. Further, in such a case where the districts to be monitored by the disease monitoring system S are developing countries, emerging countries, and the like, the communication infrastructures of the entirety of the districts may not have sufficiently been developed. Also in this case, if the base station 3 is installed within a range that allows wireless communication with the facility where the sample analyzing apparatus 1 is installed, the transmission information totaled in the sample analyzing apparatus 1 can be transmitted to the receiving apparatus 2.

According to the present embodiment, appropriateness of the presence or absence of the three major diseases inputted via the input screen D1 is determined based on the measurement result obtained by the sample analyzing apparatus 1. Then, when the inputted presence or absence of the three major diseases is not appropriate, the alarm screen D3 is displayed on the display input unit 11. That is, in a case where the operator has inputted, via the input screen D1, "negative" by mistake when the operator should have inputted "positive", and in a case where the operator has inputted "positive" by mistake when the operator should have inputted "negative", the alarm screen D3 is displayed. Accordingly, occurrence of erroneous input of the presence or absence of the three major diseases can be suppressed, and thus, a situation can be prevented where transmission information is created based on incorrect presence or absence of the three major diseases and the created transmission information is transmitted to the receiving apparatus 2.

According to the present embodiment, on the confirmation screen D2 of the display input unit 11, the area D22 for indicating the measurement result of blood cells, and the area D23 for indicating the presence or absence of the three major diseases are displayed. Accordingly, the operator (such as a medical doctor) of the sample analyzing apparatus 1 can compare and check the measurement result and the presence or absence of the three major diseases, thereby being able to more appropriately determine a disease of the patient based on the measurement result, or the appropriateness of the presence or absence of the disease.

According to the present embodiment, transmission information created based on the presence or absence of the three major diseases is transmitted from the sample analyzing apparatus 1 to the receiving apparatus 2. Therefore, for example, in a case where the receiving apparatus 2 is installed in an agency, such as a government agency, that comprehensively controls districts, the controlling agency can promptly and efficiently understand the infection states of the three major diseases.

According to the present embodiment, the receiving apparatus 2 calculates the positive rates of the three major diseases for each district, from the transmission information received from the sample analyzing apparatus 1, and in the table D42 on the confirmation map screen D4, the calculated positive rates are displayed. Accordingly, the operator of the receiving apparatus 2 can properly understand the infection states of the three major diseases.

According to the present embodiment, in a case where there is a disease whose positive rate is greater than or equal to the threshold Sh1 and whose total number of samples is greater than or equal to the threshold Sh2, an alarm indicating that the disease is in an epidemic state is displayed in the comment on the confirmation map screen D4. Accordingly, the operator of the receiving apparatus 2 can properly understand the urgency of taking countermeasures against the disease. Moreover, in the comment on the confirmation map screen D4, the total number of samples used in calculation of the positive rate of the disease is displayed. Accordingly, the operator can determine whether the reliability of the alarm is high or not.

According to the present embodiment, on the confirmation map screen D4, the table D42 including the positive rates is displayed along with the map D43. Accordingly, the operator of the receiving apparatus 2 can visually confirm the place of the district where the disease is in epidemic state, and the geographically expanding direction of the disease and the like.

According to the present embodiment, transmission information created in the sample analyzing apparatus 1 includes the number of positive samples and the total number of samples for each of the three major diseases. Accordingly, the receiving apparatus 2 can calculate the positive rate from the number of positive samples and the total number of samples, based on the received transmission information. It should be noted that transmission information created in the sample analyzing apparatus 1 may include the number of positive samples and the number of negative samples for each of the three major diseases. Also in this case, the receiving apparatus 2 can calculate the total number of samples from the number of positive samples and the number of negative samples based on the received transmission information, and thus, can calculate the positive rates as in the present embodiment.

An embodiment of the present invention has been described above. However, the embodiment of the present invention is not limited thereto.

For example, in the above embodiment, the sample analyzing apparatus 1 is an apparatus that counts blood cells in blood. However, the present invention is not limited thereto. The sample analyzing apparatus 1 may be a blood coagulation analyzing apparatus that performs analysis regarding coagulability of blood. Further, the sample analyzing apparatus 1 may be an apparatus that measures only the number of white blood cells and that does not classify the white blood cells. Further, the sample analyzing apparatus 1 may be an apparatus that analyzes any clinical sample as a sample. For example, the sample analyzing apparatus 1 may be an immune analyzing apparatus or a biochemical analyzing apparatus that measures serum, a urine analyzing apparatus that analyzes urine, or an analyzing apparatus that analyzes bone marrow aspirate. Further, the sample analyzing apparatus 1 may be an apparatus that can determine the presence or absence of one or two of the three major diseases.

Figure 13:
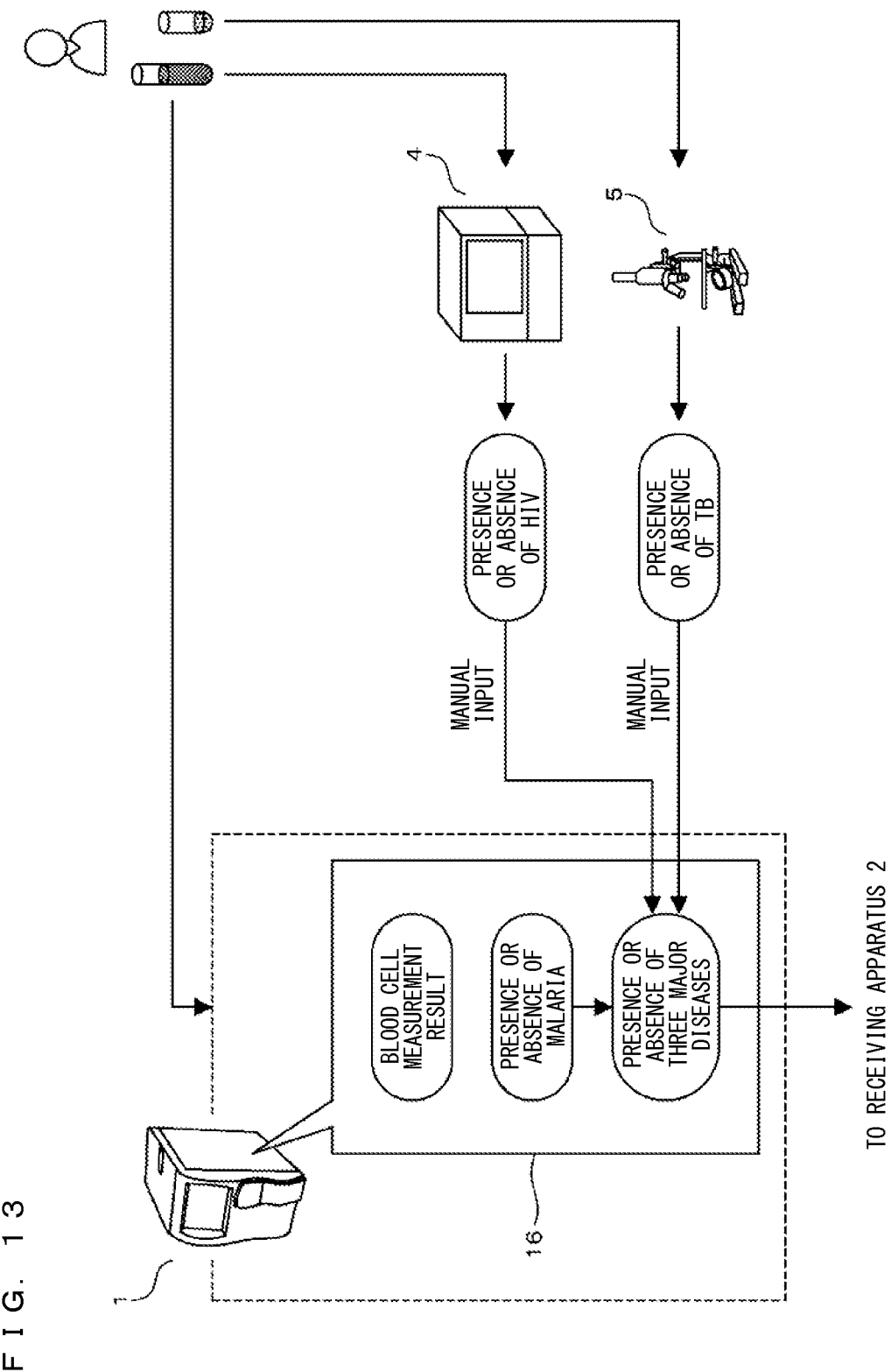
FIG. 13 shows the routes in which the presence or absence of the three major diseases is stored in a sample analyzing apparatus according to a modification.

FIG. 13 shows the routes in which the presence or absence of the three major diseases is stored in the sample analyzing apparatus 1 in a modification where the sample analyzing apparatus 1 is an apparatus capable of determining the presence or absence of malaria.

According to this modification, in the sample analyzing apparatus 1, the presence or absence of malaria is determined based on a measurement result, and the obtained presence or absence of malaria is directly stored in the hard disk 16. In this case, in the sample analyzing apparatus 1, the specimen preparation unit 12 prepares a measurement specimen for detecting malaria-infected red blood cells, and based on this measurement specimen, the WBC measurement unit 13 performs measurement. Specifically, as shown in FIG. 14A, the CPU 101 creates a scattergram based on forward scattered light signals and side fluorescence signals obtained by the WBC measurement unit 13. Then, the CPU 101 demarcates, in this scattergram, malaria-infected red blood cells from other cell groups, thereby determining the presence or absence of malaria.

Then, the presence or absence of HIV obtained by the apparatus 4 and the presence or absence of TB obtained by use of the fluorescence microscope 5 are inputted via the display input unit 11 of the sample analyzing apparatus 1 as in the above embodiment, and are stored into the hard disk 16. Thus, in the hard disk 16, a result table similar to that of the above embodiment is stored. Here, in the input screen D1, the area D15 for indicating the presence or absence of malaria is displayed in the area D12 for indicating the measurement result, and the buttons D15a to D15c are omitted. Similarly, in the confirmation screen D2, the presence or absence of malaria that has been in the area D23 is now displayed in the area D22.

FIG. 14B is a flow chart showing the measurement process of this case. Here, in the measurement process of the above embodiment shown in FIG. 9A, S41 is added between S3 and S4, and S42 is added instead of S5. In S3, in addition to the measurement similar to that in the above embodiment, measurement for detecting malaria-infected red blood cells is performed. Subsequently, the CPU 101 performs demarcation, as shown in FIG. 14A, to determine the presence or absence of malaria (S41). Then, the CPU 101 adds a record in the result table (S4), and stores, in this record, the sample ID, the measurement result, the measurement date and time, and the presence or absence of malaria (S42).

According to the present modification, even in a case where equipment capable of diagnosing malaria is not installed in a facility, it becomes possible to obtain the presence or absence of malaria by the sample analyzing apparatus 1. Moreover, while the presence or absence of malaria is obtained by this sample analyzing apparatus 1, the presence or absence of HIV and the presence or absence of TB can further be inputted via the input screen D1 into the sample analyzing apparatus 1. Moreover, as in the above embodiment, the sample analyzing apparatus 1 can provide the receiving apparatus 2 with transmission information based on the presence or absence of the three major diseases stored in the hard disk 16.

In the present modification, via the input screen D1, only the presence or absence of HIV and the presence or absence of TB can be inputted. However, the presence or absence of malaria may further be inputted. In this case, as in the above embodiment, the presence or absence of malaria obtained by use of the fluorescence microscope 6 is inputted via the display input unit 11. As a result, the presence or absence of malaria can be obtained both by the sample analyzing apparatus 1 and the fluorescence microscope 5, and thus, reliability of the presence or absence of malaria can be increased.

According to the above embodiment, in the sample analyzing apparatus 1, transmission information shown in FIG. 6B is created. However, the present invention is not limited thereto. Transmission information shown in FIG. 14C may be created from the result table. In this case, from the transmission process shown in FIG. 10B, the process of S22 is omitted. Then, in S23 of FIG. 10B, transmission information including the raw records extracted from the result table as shown in FIG. 14C is created.

FIG. 14D is a flow chart showing the reception process of this case. Here, in the reception process of the above embodiment shown in FIG. 11A, S103 is omitted and S201 and S202 are added, instead.

Upon receiving transmission information (S102: YES), the CPU 201 of the receiving apparatus 2 calculates the number of positive samples and the total number of samples for each of the three major diseases from the received transmission information, to create totaled information (S201). That is, the CPU 201 totals the presence or absence for each of the three major diseases for each identification information included in the received transmission information, and creates totaled information corresponding to the transmission information shown in FIG. 6B. Then, the CPU 201 stores the created totaled information in the reception table (S202). It should be noted that in a case where the transmission information shown in FIG. 14C is created, at the timing where the presence or absence of the three major diseases and the input date and time have been stored in the result table, transmission information may be immediately created and transmitted to the receiving apparatus 2. Accordingly, the receiving apparatus 2 becomes able to instantaneously understand the morbidity states of the three major diseases.

In the above embodiment, when the presence or absence of the three major diseases inputted via the display input unit 11 is inappropriate, the alarm screen D3 is displayed. Moreover, in the receiving apparatus 2, the alarm indicating that any of the three major diseases is in an epidemic state is displayed in the comment in the table D42. However, the present invention is not limited thereto, and the alarm may be notified to the operator by other means (for example, an alarm sound outputted from a speaker).

Further, in the above embodiment, based on the positive rate and the total number of samples, the alarm indicating an epidemic state is displayed. Instead of this, if there is a disease whose positive rate is greater than or equal to the threshold Sh1, an alarm indicating that this disease is in an epidemic state may be displayed in the receiving apparatus 2. Moreover, if there is a disease whose number of positive samples is greater than or equal to a threshold Sh3, an alarm indicating that this disease is in an epidemic state may be displayed in the receiving apparatus 2. Moreover, in the above embodiment, in the table D42 on the confirmation map screen D4, the number of positive samples and the number of negative samples calculated for each of the three major diseases may be displayed in combination, for each district.

In the above embodiment, the result table and the transmission information are each configured as shown in FIGS. 6A and 6B. However, the present invention is not limited thereto. As shown in FIG. 15A, in the result table, the sex and the age corresponding to each sample may further be stored. As shown in FIG. 15B, in addition to the number of positive samples and the total number of samples of each of the three major diseases, the transmission information of this case may include: for each disease, with regard to subjects who are positive, the number of males, the average age of the males, the number of females, and the average age of the females; and with regard to subjects included as the total number of samples for each disease, the number of males, the average age of the males, the number of females, and the average age of the females. Accordingly, the operator of the receiving apparatus 2 can confirm the number of males and females having a disease in an epidemic state, the ratio of the males and the females, the average ages thereof, and the like. Thus, the operator can know further in detail the infection states in the entirety of the districts (country in the case of the present embodiment) to be monitored by the disease monitoring system S.

It should be noted that sex and age may be inputted by the operator via the display input unit 11 when a measurement order is created in the sample analyzing apparatus 1. In a case where the sample analyzing apparatus 1 is connected to a host computer for managing measurement orders, the sample analyzing apparatus 1 may obtain, from the host computer, sex and age in addition to the measurement order. Moreover, the transmission information of this case includes both of sex and age, but may include either one of sex and age. As transmission information to be transmitted to the receiving apparatus 2 performing management, count results regarding the sample obtained by measurement units of the sample analyzing apparatus 1 may be sent to the receiving apparatus 2 in an external facility, along with the presence or absence of the three major diseases. In such a case, the receiving apparatus 2 can understand the states of the diseases further in detail.

In the above embodiment, the transmission process is performed as shown in FIG. 10B, but may be performed as shown in FIGS. 16A and 16B, instead. FIG. 16A is equivalent to the flow chart of FIG. 10B from which S21 is omitted and to which S301 to S303 are added, instead. FIG. 16B shows another transmission process performed in parallel with the transmission process of FIG. 16A, and is started simultaneously with the transmission process of FIG. 16A.

With reference to FIG. 16A, the CPU 201 of the receiving apparatus 2 starts counting time, first (S301). Subsequently, the CPU 201 determines, based on the counted time, whether a predetermined time period (for example, two hours) has elapsed (S302). When the predetermined time period has elapsed (S302: YES), the CPU 201 determines whether there is a sample that has not yet been transmitted (S303). When there is no sample that has not yet been transmitted (S303: NO), the CPU 201 returns the process to S301. On the other hand, when there is a sample that has not yet been transmitted (S303: YES), the CPU 201 performs the processes of S22 to S24 as in the above embodiment, and then returns the process to S301. On the other hand, with reference to FIG. 16B, upon receiving a shutdown instruction (S311: YES), the CPU 201 determines whether there is a sample that has not yet been transmitted (S312). When there is a sample that has not yet been transmitted (S312: YES), the CPU 201 performs the processes of S313 to S315, as in S22 to S24. When the transmission processes are performed as shown in FIGS. 16A and 16B, compared with the above embodiment, the infection states of the three major diseases can be assuredly and automatically provided to the receiving apparatus 2. Moreover, the agency, such as a government agency, that comprehensively controls the districts can understand the infection states of the three major diseases in a timely manner, compared with the above embodiment.

Moreover, the transmission processes may be performed as shown in FIGS. 16B and 16C. FIG. 16C is equivalent to the flow chart shown in FIG. 16A from which S301 is omitted and to which S401 is added instead of S302. In this case, in S401, the CPU 201 determines whether the current time has become a predetermined time (for example, 0 o'clock). When it has been determined as YES in S401, the processes of S303, and S22 to S24 are performed as in FIG. 16A.

Further, the transmission processes may be performed as shown in FIGS. 16B and 16D. FIG. 16D is equivalent to the flow chart shown in FIG. 16A from which S301 is omitted and to which S501 is added instead of S302 and S303. In this case, in S501, the CPU 201 determines whether the number of samples that have not yet been transmitted has become greater than or equal to a predetermined number. When it has been determined as YES in S501, the processes of S22 to S24 are performed as in FIG. 16A. When the transmission processes are performed as shown in FIGS. 16B and 16D, for example, also in a case where the number of persons infected with the three major diseases is rapidly increasing, the infection states are transmitted to the receiving apparatus 2 at a high frequency. Thus, the agency, such as a government agency, that comprehensively controls the districts, can appropriately understand that infection of the three major diseases is expanding, and can take appropriate countermeasures.

Further, in the above embodiment, the presence or absence of the three major diseases is inputted manually by the operator, via the input screen D1 displayed on the display input unit 11. However, the present invention is not limited thereto. In a case where the apparatus 4 is communicably connected to the sample analyzing apparatus 1, the presence or absence of HIV may be transmitted from the apparatus 4 to the sample analyzing apparatus 1, and the transmitted presence or absence of HIV may be stored in the hard disk 16. Also, in a case where an apparatus capable of performing diagnosis on the presence or absence of TB and an apparatus capable of performing diagnosis on the presence or absence of malaria are communicably connected to the sample analyzing apparatus 1, the transmitted presence or absence of TB and the transmitted presence or absence of malaria may be stored in the hard disk 16.

Further, in the above embodiment, on the paper sheet discharged from the opening 1d of the sample analyzing apparatus 1, the presence or absence of the three major diseases may be printed in addition to the measurement result by the sample analyzing apparatus 1. Accordingly, as in the case of the confirmation screen D2 displayed on the display input unit 11, the operator can confirm the measurement result and the presence or absence of the three major diseases in combination.

What is claimed is:

1. A sample analyzing apparatus comprising:
   a detector that measures blood cells in a sample obtained from a subject so as to count the blood cells to produce a measurement result comprising a count result of the blood cells for the sample;
   an input unit that receives a manual input of one or more externally obtained diagnosis results of a presence or absence of a disease for the sample;
   a memory in which the count result of the blood cells for the sample, and the manual input of one or more externally obtained diagnosis results for the sample, are both stored in association with the sample;
   a communication transmitter that transmits disease information based on the presence or absence of the disease stored in the memory in association with the sample, over a communication link to a receiving apparatus installed in an external facility; and
   a processor coupled to the detector, the memory, and the communication transmitter, the processor executing a computer program stored in the memory, the processor configured by the computer program to perform operations to:
   control and to receive signals from the detector and to process the received signals; and
   compare the manually inputted one or more externally obtained diagnosis results of the presence or absence of the disease with the count result obtained by the detector.

2. The sample analyzing apparatus of claim 1, wherein the processor is further configured by the computer program to perform operations to receive the manual input of the one or more externally obtained diagnosis results of the presence or absence of the disease.

3. The sample analyzing apparatus of claim 1, wherein the processor is further configured by the computer program to perform operations to determine the presence or absence of the disease regarding the sample, based on the measurement result obtained by the detector.

4. The sample analyzing apparatus of claim 3, wherein the processor is further configured to perform operations to when having determined that the inputted one or more manual determinations of the presence or absence of the disease is incorrect, cause a predetermined alarm.

5. The sample analyzing apparatus of claim 1, wherein the communication transmitter transmits the disease information to the receiving apparatus, every time a predetermined period has elapsed.

6. The sample analyzing apparatus of claim 1, wherein when a number of pieces of the disease information that have not yet been transmitted to the receiving apparatus has reached a predetermined number, the communication transmitter transmits, to the receiving apparatus, the pieces of the disease information that have not yet been transmitted.

7. The sample analyzing apparatus of claim 1, wherein the communication transmitter transmits, along with the disease information, location information regarding a location where the sample analyzing apparatus is installed, to the receiving apparatus.

8. The sample analyzing apparatus of claim 1, wherein the disease is HIV/AIDS, tuberculosis, or malaria.

9. The sample analyzing apparatus of claim 1, wherein the communication transmitter performs wireless communication with a communication network to which the receiving apparatus is connected.

10. The sample analyzing apparatus of claim 1, further comprising
    a display coupled to the processor, wherein
    the processor is further configured to perform operations to cause the display to display the measurement result along with the presence or absence of the disease.

11. The sample analyzing apparatus of claim 1, wherein the communication transmitter transmits the count result of the count of the blood cells along with the disease information, to the receiving apparatus installed in the external facility.

12. A disease monitoring system comprising:
    a plurality of the sample analyzing apparatuses of claim 1; and
    a plurality of the receiving apparatuses.

13. The disease monitoring system of claim 12, wherein each of the plurality of the receiving apparatuses comprises a display, and
    each of the plurality of the receiving apparatuses comprises a processor executing a stored computer program, the processor configured by the computer program to perform operations to
    calculate a total of the number of positive samples or to calculate a positive rate regarding the disease based on the disease information received from the sample analyzing apparatus, and
    cause the display to display the number of positive samples or the positive rate on the display.

14. The disease monitoring system of claim 13, wherein the processor is further configured to perform an operation to provide an alarm when the number of positive samples or the positive rate is greater than or equal to a predetermined value.

15. The disease monitoring system of claim 13, wherein the processor is further configured to perform an operation to provide an alarm when the number of positive samples is greater than or equal to a predetermined value and the positive rate is greater than or equal to a predetermined value.

16. The disease monitoring system of claim 13, wherein the processor is further configured to perform an operation to calculate a total of the number of positive samples or to calculates the positive rate, for each district where the respective one of the plurality of sample analyzing apparatuses is located.

17. The disease monitoring system of claim 16, wherein the processor is further configured to perform an operation to cause the number of positive samples or the positive rate to be displayed on the display in combination with a map.

18. The disease monitoring system of claim 12, wherein the processor of each of the plurality of sample analyzing apparatuses is further configured to perform operations to transmit the disease information to a respective one of the plurality of receiving apparatuses when determination of the disease regarding the sample is positive, and when determination of the disease regarding the sample is negative.

19. The disease monitoring system of claim 12, wherein the processor of each of the plurality of sample analyzing apparatuses is further configured to perform operations to transmit the disease information and information indicating one of: a sex and an age of each subject from whom a sample has been obtained to a respective one of the plurality of receiving apparatuses.

20. The sample analyzing apparatus of claim 1, wherein the processor is further configured by the computer program to perform operations to determine whether the manually inputted one or more externally obtained diagnosis results of the presence or absence of the disease is incorrect based on the measurement result obtained by the detector such that:
when a value of the measurement result obtained by the detector is outside of an expected range of values when a presence of the disease is determined, the manually inputted one or more externally obtained diagnosis results of the presence of the disease is determined to be incorrect; and
when a value of the measurement result obtained by the detector is outside of an expected range of values when an absence of the disease is determined, the manually inputted one or more externally obtained diagnosis results of the absence of the disease is determined to be incorrect.

21. A method for managing data of a sample analyzing apparatus comprising a processor executing a computer program, a communication transmitter, a detector that measures a sample, an input unit, and a memory, the method comprising:
measuring, by the detector, blood cells in the sample so as to count the blood cells to produce a measurement result comprising a count result of the blood cells for the sample;
obtaining, by the processor from the input unit, a manual input of one or more externally obtained diagnosis results of a presence or absence of a disease for the sample;
storing, in the memory, both the count result of measuring the blood cells, and the one or more manual inputs of the one or more respective externally obtained diagnosis results in association with the sample;
compare the manually inputted one or more externally obtained diagnosis results of the presence or absence of the disease with the count result obtained by the detector; and
transmitting, by the communication transmitter, disease information based on the presence or absence of the disease to a receiving apparatus installed in an external facility.

* * * * *